US008454358B2

(12) United States Patent
Wahab

(10) Patent No.: US 8,454,358 B2
(45) Date of Patent: *Jun. 4, 2013

(54) TOOTH POSITIONERS, METHOD OF MAKING THE SAME, AND METHOD OF POSITIONING TEETH USING THE SAME

(76) Inventor: Waqas Wahab, Lahore (PK)

( * ) Notice: Subject to any disclaimer, the term of this patent is extended or adjusted under 35 U.S.C. 154(b) by 0 days.

This patent is subject to a terminal disclaimer.

(21) Appl. No.: 13/406,741

(22) Filed: Feb. 28, 2012

(65) Prior Publication Data

US 2012/0156633 A1 Jun. 21, 2012

Related U.S. Application Data

(63) Continuation of application No. 12/204,894, filed on Sep. 5, 2008, now Pat. No. 8,152,522.

(60) Provisional application No. 60/970,677, filed on Sep. 7, 2007.

(51) Int. Cl.
*A61C 3/00* (2006.01)

(52) U.S. Cl.
USPC .............................................. 433/24; 433/215

(58) Field of Classification Search
USPC ................. 433/24, 213, 215, 6, 74, 214, 167, 433/53, 223
See application file for complete search history.

(56) References Cited

U.S. PATENT DOCUMENTS

| 4,371,339 | A | 2/1983 | Zeiser | |
|---|---|---|---|---|
| 6,572,372 | B1 * | 6/2003 | Phan et al. | 433/6 |
| 2006/0093982 | A1 | 5/2006 | Wen | |
| 2006/0275736 | A1 | 12/2006 | Wen | |
| 2008/0206702 | A1 | 8/2008 | Hedge et al. | |

OTHER PUBLICATIONS

International Search Report dated Dec. 1, 2008.

* cited by examiner

*Primary Examiner* — Sunil K Singh
(74) *Attorney, Agent, or Firm* — Antonelli, Terry, Stout & Kraus, LLP.

(57) ABSTRACT

A method for forming a tooth positioner for repositioning at least one tooth of a patient includes providing a dental arch cast of a patient, separating at least one tooth from the dental arch cast, fixing a pin in a stump part of the at least one separated tooth, and in any non-separated teeth, reconstructing the dental arch cast of the patient by aligning the separated teeth to correspond to the alignment in the patient's mouth and holding the pins in a material that may be softened by heat, heating an area to soften an area, applying force to the pin fixed in the at least one tooth to be repositioned to move it in a desired direction to obtain a realigned arch, and forming a tooth positioner corresponding to the realigned arch. The tooth positioner is used by having the patient wear it for a period of time.

3 Claims, 27 Drawing Sheets

TOOTH POSITIONERS, METHOD OF MAKING THE SAME, AND METHOD OF POSITIONING TEETH USING THE SAME

CROSS-REFERENCE TO RELATED APPLICATION

This application is a continuation application of application Ser. No. 12/204,894 filed Sep. 5, 2008 now U.S. Pat. No. 8,152,522, which is a nonprovisional application of and claims benefit of the filing date of provisional application No. 60/970,677, filed Sep. 7, 2007, the contents of which are incorporated herein by reference in their entireties.

BACKGROUND OF THE INVENTION

Orthodontics is the branch of dentistry that specializes in the diagnosis, prevention and treatment of the dental and facial irregularities. The technical term for these problems is "malocclusion."

Malocclusions can be treated by treatment modalities using fixed or removable appliances, or a combination of both. Fixed appliances are known as braces, and they are most common form of treatment for malocclusion. Braces involve moving teeth into desired position through a system of brackets and wires that apply pressure on teeth and shift in a certain direction. Conventional removable appliances are composed of wires attached to a plastic/polymer base and can be removed by the patient. Malocclusions can also be corrected with the removable appliance named as "aligners," "tooth positioners" or "correctors."

A tooth positioner is a clear and removable orthodontic appliance.

Tooth positioners were developed over 50 years ago and are made of clear plastic to guide teeth after fixed braces therapy or for minor adjustment of the teeth.

SUMMARY OF THE INVENTION

A method for forming a tooth positioner for repositioning at least one tooth of a patient includes providing a dental arch cast of a patient having at least one tooth to be repositioned, separating at least one tooth from the dental arch cast, including the at least one tooth to be repositioned to provide at least one separated cast tooth having a crown part and a stump representing a root, fixing a pin in the stump part of the at least one separated tooth, and in any non-separated teeth, each of the pins extending outwardly from the stump part, reconstructing the dental arch cast of the patient by aligning the separated teeth to correspond to the alignment in the patient's mouth and holding the pins in a material that may be softened by heat, heating at least an area of the material that may be softened by heat in which the pin fixed in the at least one tooth to be repositioned is held to soften the area, applying force to at least the pin fixed in the at least one tooth to be repositioned to move the at least one tooth to be repositioned in a desired direction to obtain a realigned arch, cooling the material that may be softened by heat; and forming a tooth positioner corresponding to the realigned arch.

The tooth positioner can be used by having the patient wear the tooth positioner for a period of time.

A method for reviewing a diagnostic setup for an orthodontic treatment, includes providing a dental arch cast of a patient having at least one tooth to be repositioned, separating at least one tooth from the dental arch cast, including the at least one tooth to be repositioned to provide at least one separated cast tooth having a crown part, and a stump representing a root, fixing a pin in the stump part of the at least one separated tooth, and in any non-separated teeth, each of the pins extending outwardly from the stump part, reconstructing the dental arch cast of the patient by aligning the separated teeth to correspond to the alignment in the patient's mouth and holding the pins in a material that may be softened by heat, taking a first photograph of the reconstructed dental arch cast, heating at least an area of the material that may be softened by heat in which the pin fixed in the at least one tooth to be repositioned is held to soften the area, applying force to at least the pin fixed in the at least one tooth to be repositioned to move the at least one tooth to be repositioned in a desired direction to obtain a realigned arch, taking a second photograph of the realigned arch, morphing the first and second photographs, and reviewing the morphed photographs to review a diagnostic setup for an orthodontic treatment.

BRIEF DESCRIPTION OF THE SEVERAL VIEWS OF DRAWINGS

FIGS. 7A and 6B show front and side views, respectively, of teeth having pins inserted in an upper zero aligner (ZA).

FIGS. 15A and 15B show front views, respectively, of the upper and lower processed arches together and the occlusion in the patient's mouth while

DETAILED DESCRIPTION OF THE PREFERRED EMBODIMENTS

This description is directed to those skilled in the orthodontics art. In this description, contributing parts and procedures that are well known to those skilled in the art or otherwise not essential to an understanding of the invention are described without any unnecessary detail to avoid any confusion. For example, before working on any dental Impression, the orthodontist should disinfect it with a disinfection solution as is known in the art. Since this disinfecting treatment is known in the art, this and similar treatments and products have not been mentioned here.

The method of the present invention will now be described with reference to the attached Figures.

Figure 1:
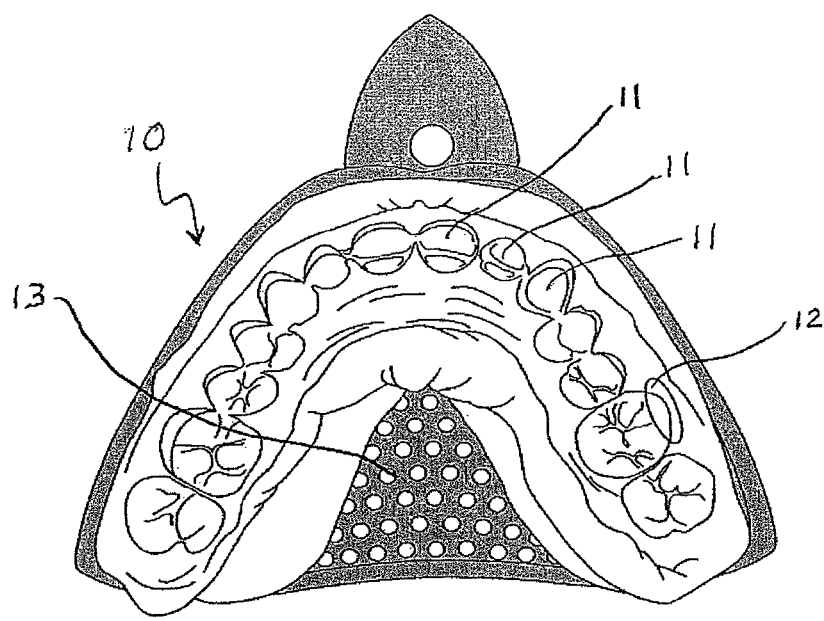
FIG. 1 shows an example of an upper impression taken in an impression tray.

Upper and lower impressions of a patient with malocclusion are taken by the doctor, e.g., dentist or orthodontist, in impression trays as shown in FIG. 1, which shows an impression 10 of the upper teeth 11 and gum 12 being taken in an impression tray 13. Impressions are poured with a casting material e.g.: epoxy resin, to make upper and lower dental arch casts, an upper cast 14 with upper cast teeth 11' being shown in FIG. 2. Epoxy is a tough synthetic resin, containing epoxy groups, that sets with specific time and further hardens when heat or pressure is applied. The casting material, e.g., epoxy resin is poured in the impression approximately 2 mm above the gum margin as shown in the circled area in FIG. 1. After the setting time as specified by the manufacturer, casts are removed from the impressions one by one. Excessive epoxy material is removed from the epoxy casts and any voids created during the casting process are filled out. This produces the exact replica of patient's teeth in the form of epoxy casts, an upper cast being shown in FIG. 2. Both the epoxy casts are placed into occlusion on any flat surface. If required, their bases are trimmed in such a way that when both arches are placed in occlusion their bases are parallel to each other.

Figure 2:
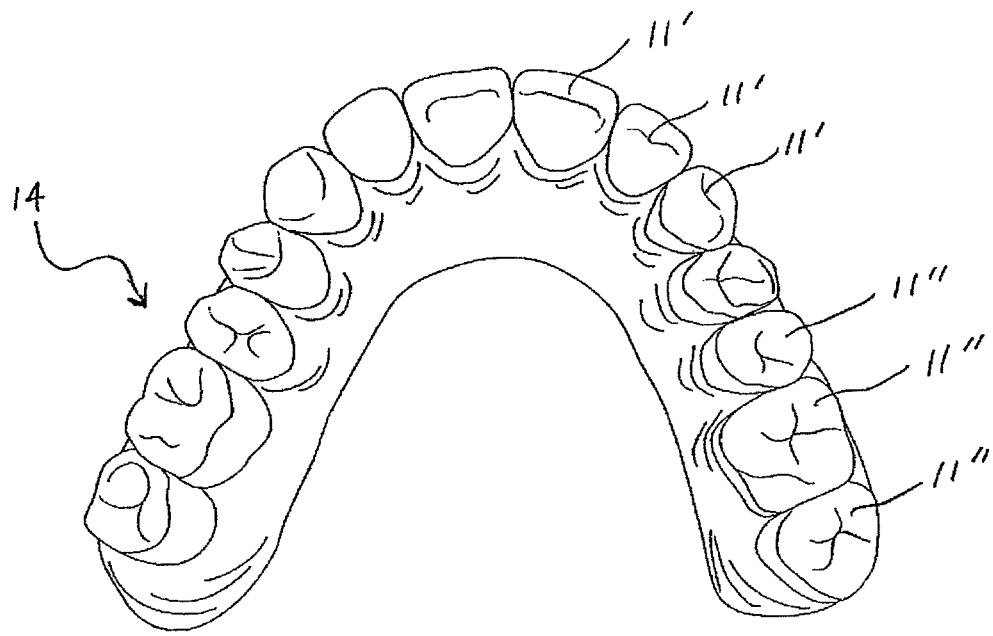
FIG. 2 shows an example of an upper epoxy cast.
Figure 3:
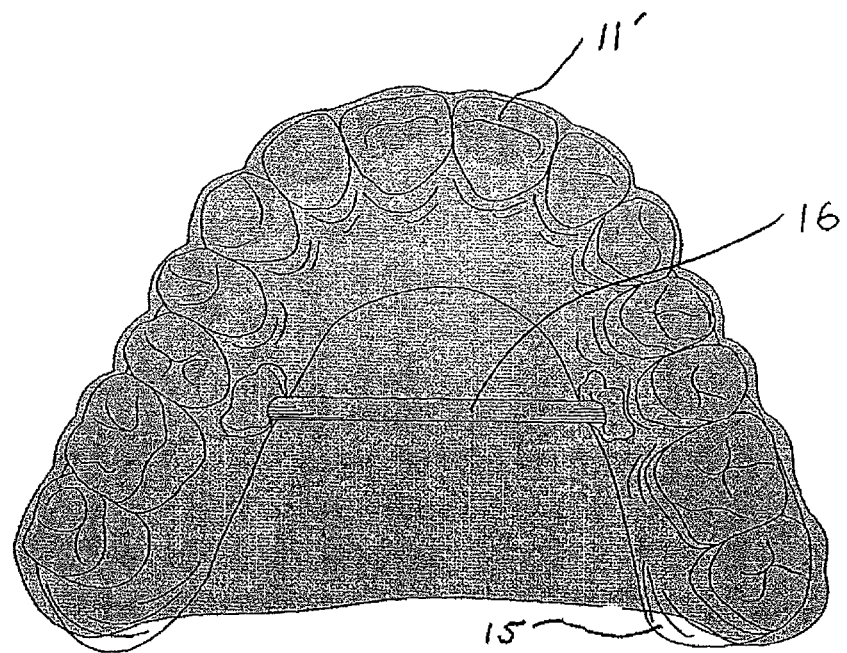
FIG. 3 shows a polymer shell made on an upper epoxy cast.

Excessive epoxy material is removed from the epoxy casts, the upper cast 14 of which is shown in FIG. 2, and any voids are filled out. Each epoxy cast, e.g., cast 14, is placed in a thermoforming machine (e.g., a Biostar thermoforming machine) to make the polymer shell 15 on it as shown in FIG. 3. In the method described herein, the polymer shell 15 is referred to as a "Zero Aligner" ("ZA"). The polymeric shells 15 fit snugly over the casts 14, thus creating a plural of the dental casts or zero aligners (ZAs). Zero aligners 15 (ZAs) are trimmed following the curves of scalloped gum line to remove all the excess plastic material around the cast, leaving about 1 mm below the gum line on buccal side, while excess material is left within the configuration of arch form. This is to give more strength to the polymeric shells to ensure the accuracy in the later process as shown in FIG. 3. Zero Aligners (ZAs) are then removed from the epoxy casts and stored to be used in the later procedures. The drawings show the manner in which the upper cast and its Zero Aligner (ZA) are made; the lower cast and its Zero Aligner (ZA) are made in a corresponding manner.

Each cast tooth 11' is then carefully separated out of epoxy casts using different cutting tools and given a tooth ID so that they are not misplaced later.

Figure 4:
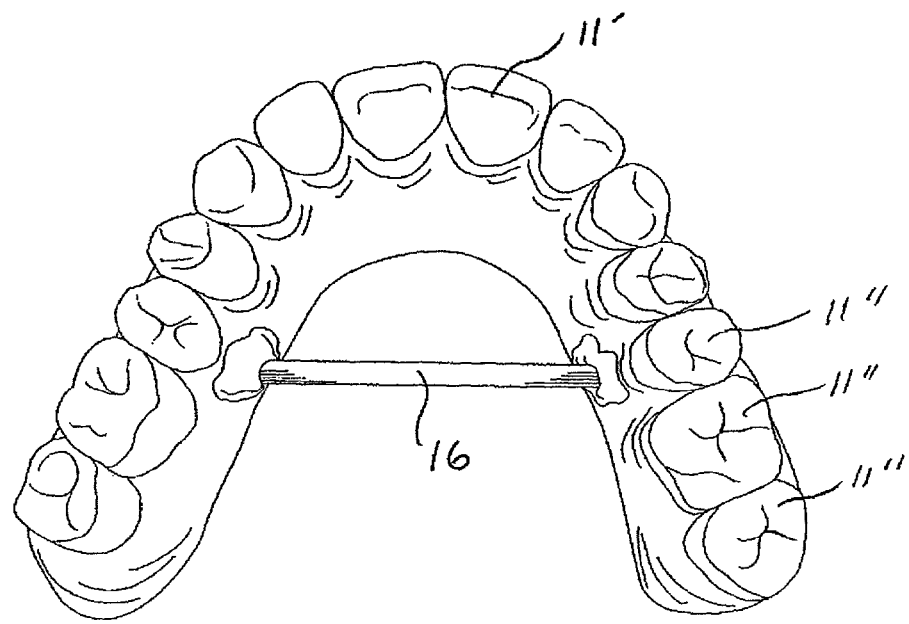
FIGS. 4 and 5 show a modified cutting technique and cast teeth separated, trimmed &finished.
Figure 5:
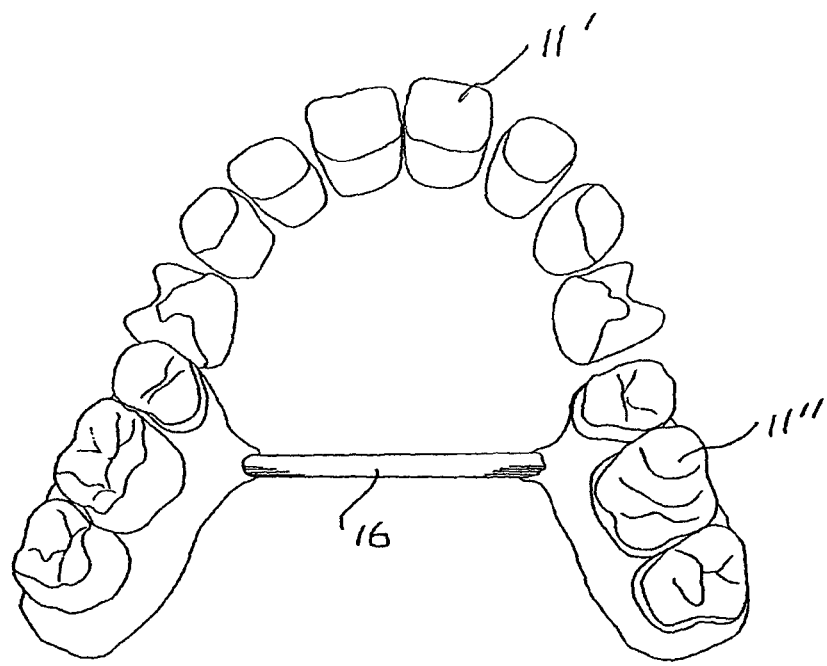
Figure 6:
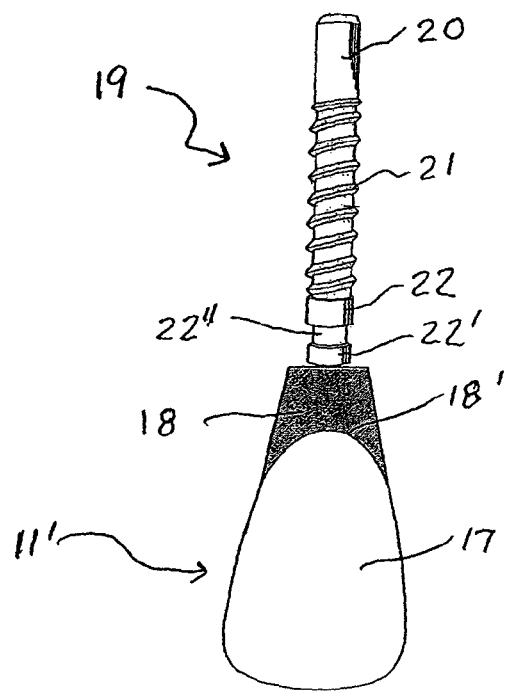
FIG. 6 shows a customized pin fixed inside a cast tooth.

A modified cutting technique, referred to herein as the butterfly technique, can be applicable in some cases. In this technique as shown in FIGS. 4 and 5, only those teeth 11' are segmented which are desired to be moved or are mal-aligned, while the rest of teeth 11" are united together, with a metal bar 16. As shown in FIGS. 4 and 5, the butterfly technique is used and a joining bar 16 connects the posterior teeth 11" with each other which are not desired to be cut.

As shown in FIG. 5, all the separated teeth 11' are trimmed and finished in such a way that at the end, a tooth crown 17 with a short stump 18 representing the root is created with a cervical margin 18' there between. The quality of the segmented teeth is verified to check if any tooth structure is lost during this process and is rebuilt if required according to the original dentition.

Holes are drilled at the base of each tooth stump 18, and in each uncut segment if the butterfly technique is used, and custom made pins 19 are inserted and fixed inside each hole by using bonding material. The pins 19 have a head 20, a threaded or corrugated body 21, first and second band parts 22 and 22', and a neck 22" there between. It can be advantageous to use a pin that has a 5 mm head 20, an 10 mm threaded or corrugated body 21, first and second band parts 22 and 22' of 2 mm and 1 mm, respectively, a neck 22" of 1 mm, and a 4 mm tail (the portion not shown within the cast tooth 11').

Figure 7A:
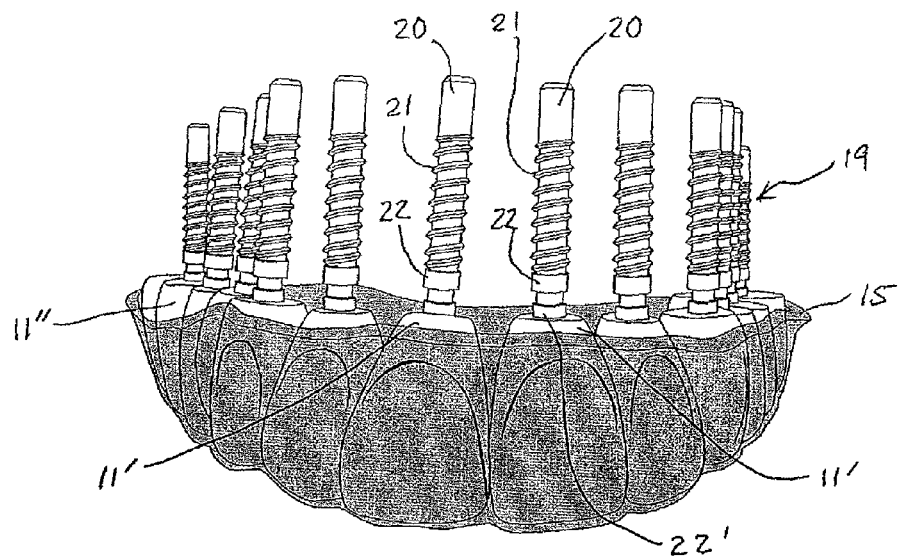
Figure 7B:
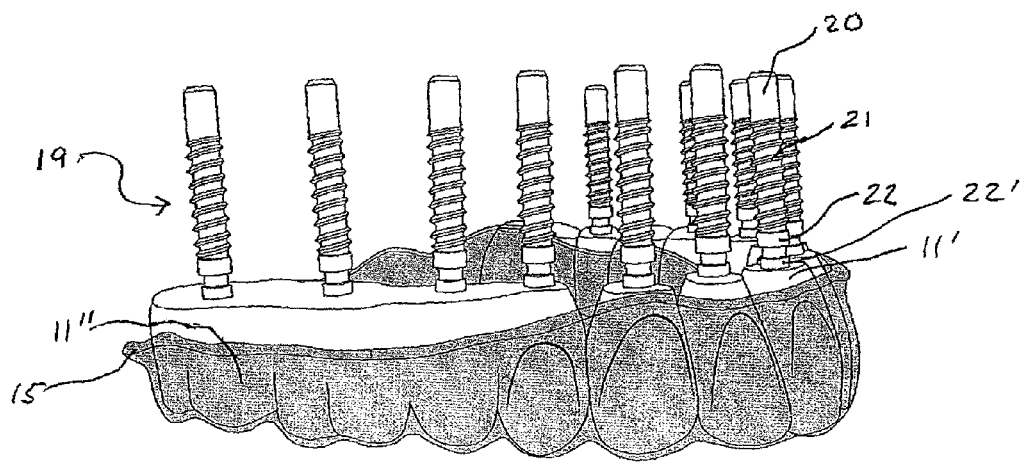

Each cut tooth/uncut segment is then manually inserted in already made zero aligners (ZAs) into their own respective position as shown in FIGS. 7A and 7B for upper arch.

Figure 8A:
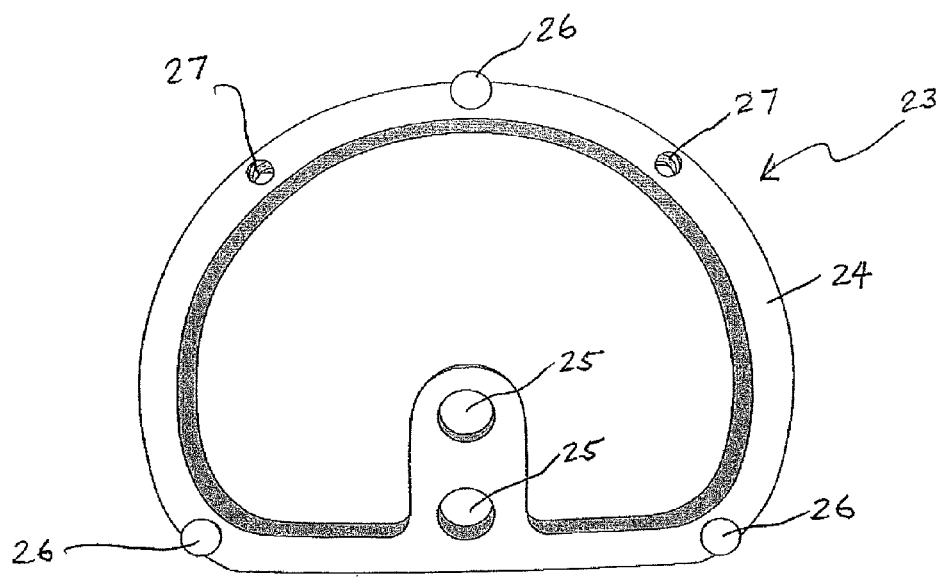
FIGS. 8A and 8B are top and perspective views, respectively, of an arch reconstruction frame (ARF).
Figure 8B:
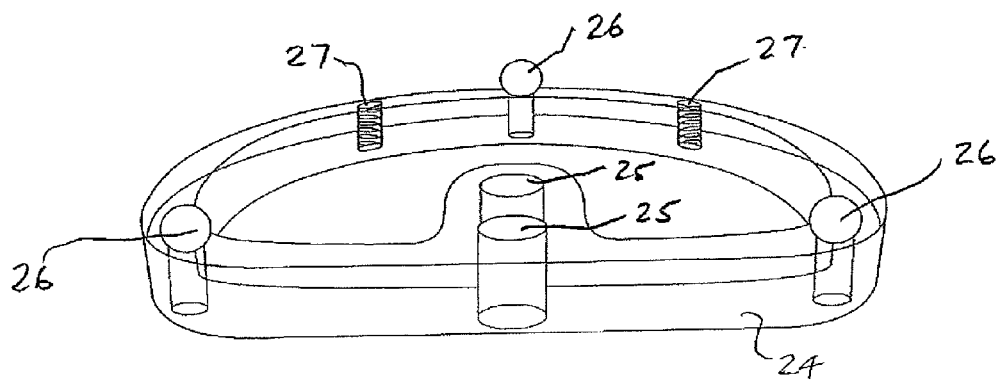
Figure 9A:
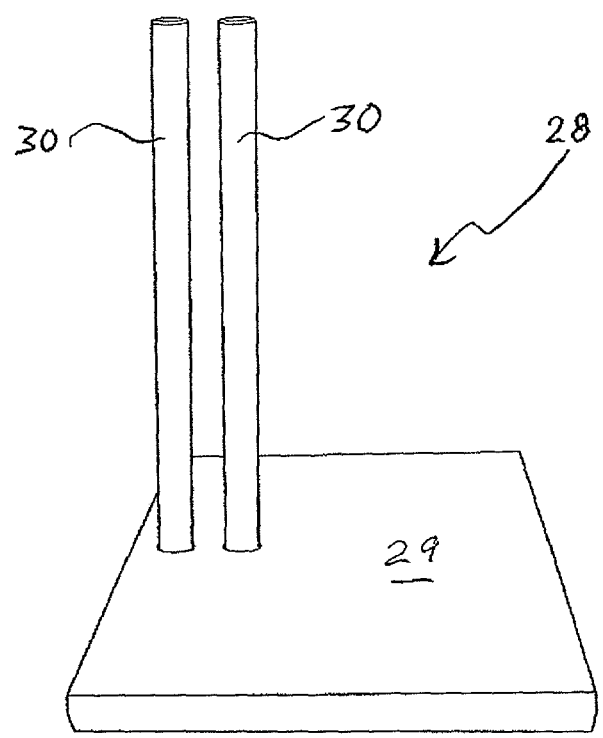
FIGS. 9A and 9B are side perspective and top perspective views, respectively, of a custom made vertical articulator.
Figure 9B:
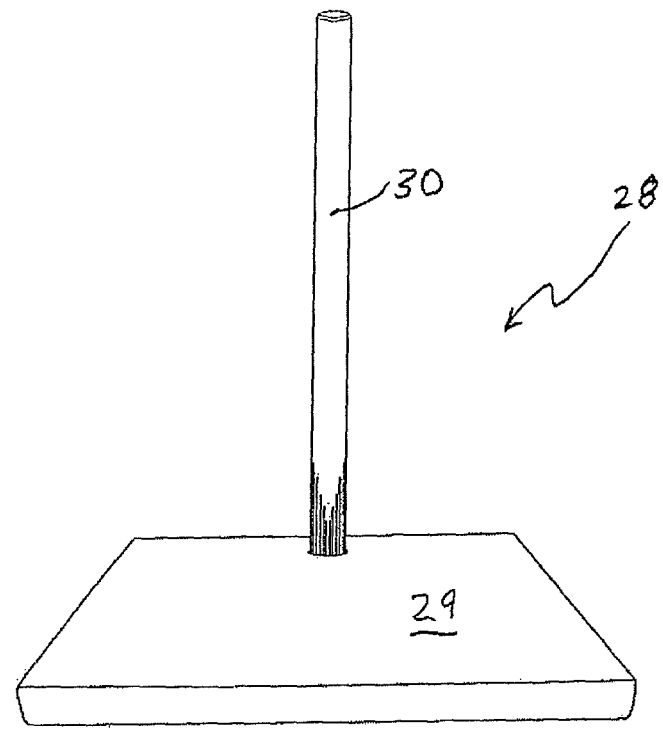
Figure 10A:
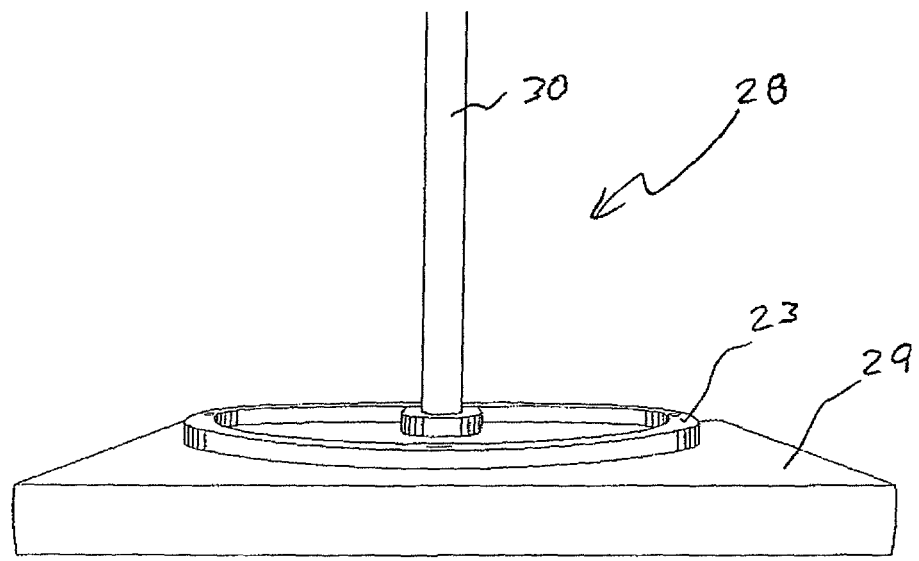
FIGS. 10A-10G show successive steps of the zeroing technique of the present invention.

A custom made frame, shown in FIGS. 8A and 8B, referred to herein as an "arch reconstruction frame" ("ARF") is placed in a custom made articulator, shown herein in FIGS. 9A and 9B, referred to herein as a "vertical articulator" ("VA") as shown in FIG. 10A.

Arch reconstruction frames (ARFs) 23 are custom made frames made up of varying materials and thickness according to their use as shown in FIGS. 8A and 8B. Each arch reconstruction frame 23 has a frame body 24 and alignment holes 25. Each arch reconstruction frame 23 may have metallic balls 26 and screw holes 27.

The vertical articulator 28, as shown in FIGS. 9A and 9B, has a base 29 and two vertical bars 30 attached to a base 29. The vertical bars 30 help to secure the arch reconstruction frames (ARFs) 23 during the arch reconstruction procedure and reloading the upper and lower arches in relation as it exists in patient's mouth (bite setting procedure).

Arch reconstruction frames (ARFs) 23 are provided on the vertical articulator 28 as shown in FIG. 10A and provide a casting boundary which holds and shapes the thermoplastic material, this thermoplastic material shaped in a horseshoe shape provides a medium for holding teeth with the help of their associated fixtures in their original as well as modified positions.

Figure 10B:
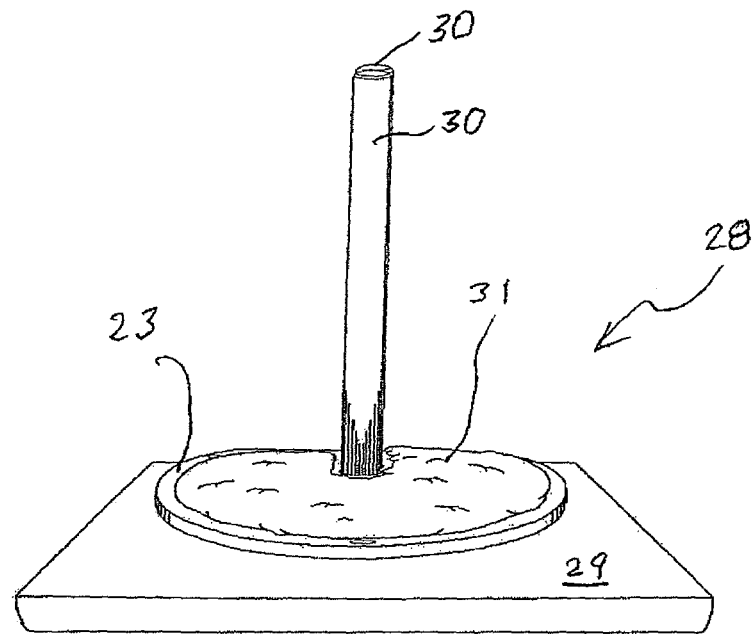

A non-sticky doughy material 31 is poured inside the arch reconstruction frame (ARF) 23 secured at the base 29 of the vertical articulator (VA) 28 as shown in FIG. 10B. One non-sticky doughy material that may be used is alginate. Alginate is a type of impression material that is used in dental practice to take the dental impressions. It is available in powder form and when mixed with water it becomes semisolid and then takes a rubbery consistency when finally set within a few minutes.

Figure 10C:
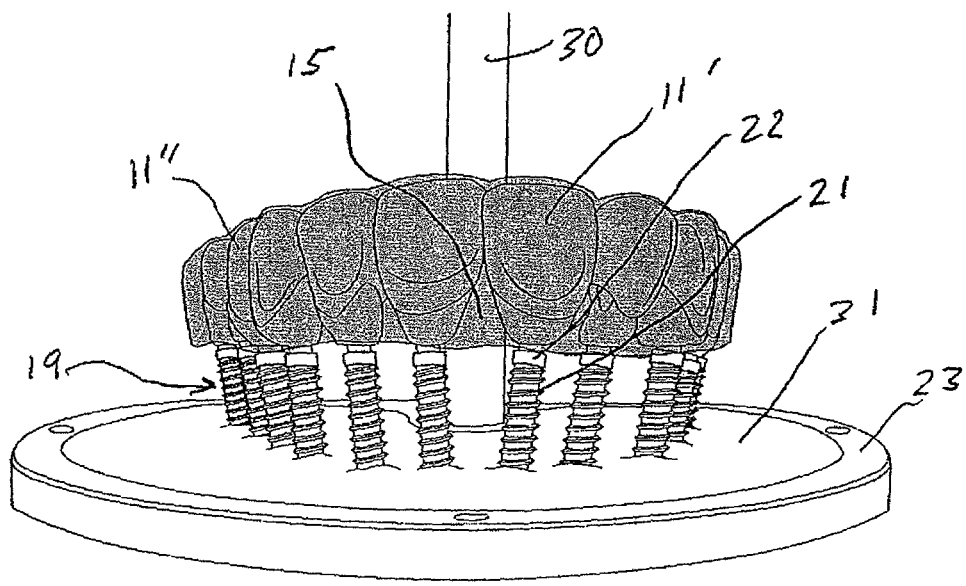

As shown in FIG. 10C, one set of cast teeth 11', 11", upper teeth in this example, along with pins 19 are placed inside the zero aligner (ZA) 15 into a freshly poured alginate impression layer 31 in such a way that heads 20 of the pins 19 dip inside the freshly poured semisolid layer alginate layer 31. After a few minutes, the alginate material layer 31 gets solidified.

Figure 10D:
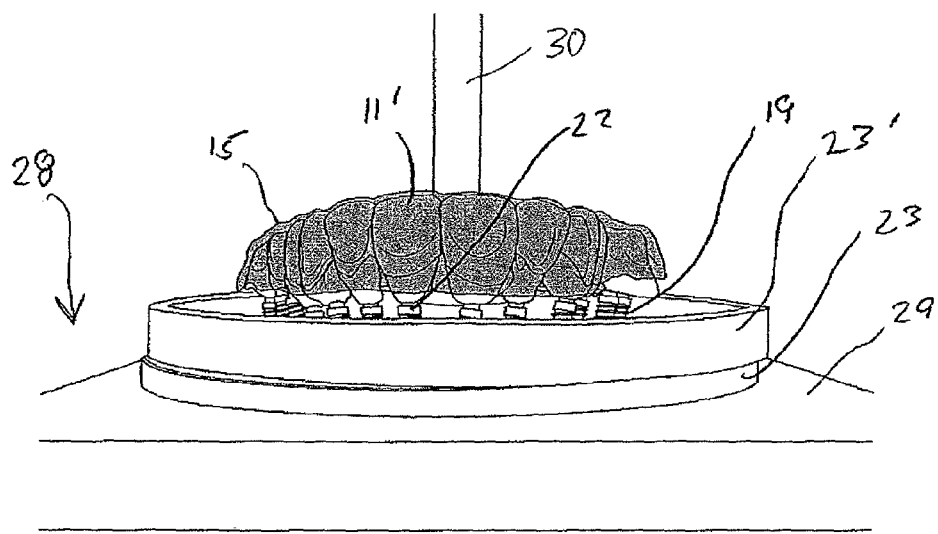
Figure 10E:
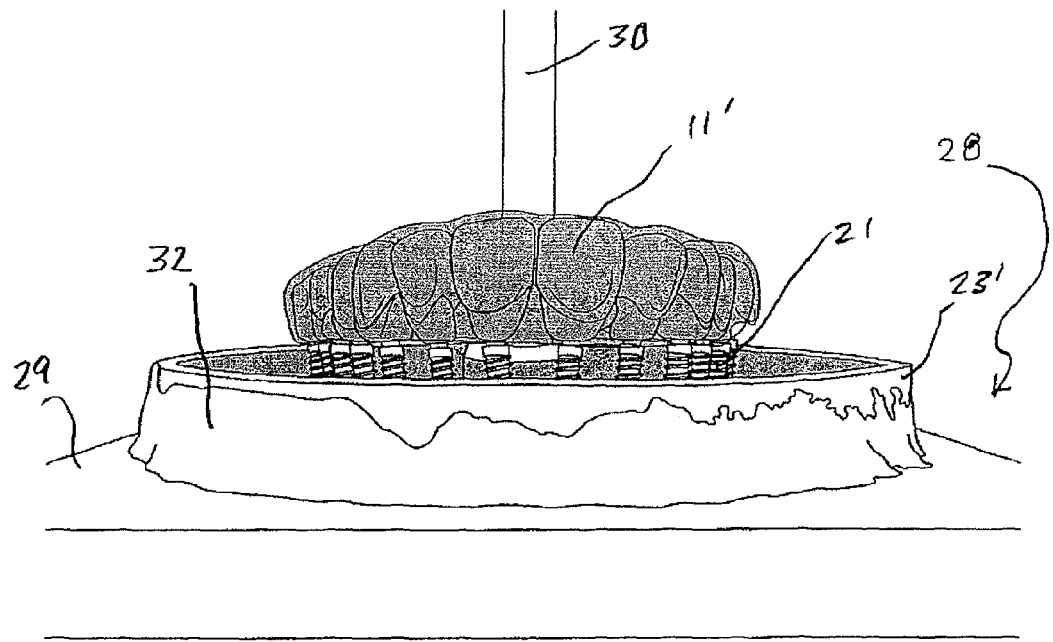

Then another arch reconstruction frame (ARF) 23' is placed on the top of already placed arch reconstruction frame (ARF) 23 in the vertical articulator 28 as shown in FIG. 10D. Any potential gaps between two arch reconstruction frames (ARFs) 23, 23' are sealed and blocked, e.g., with any block out material. Alginate/Silicone material 32 is used to fulfill this purpose as shown in FIG. 10E.

Figure 10F:
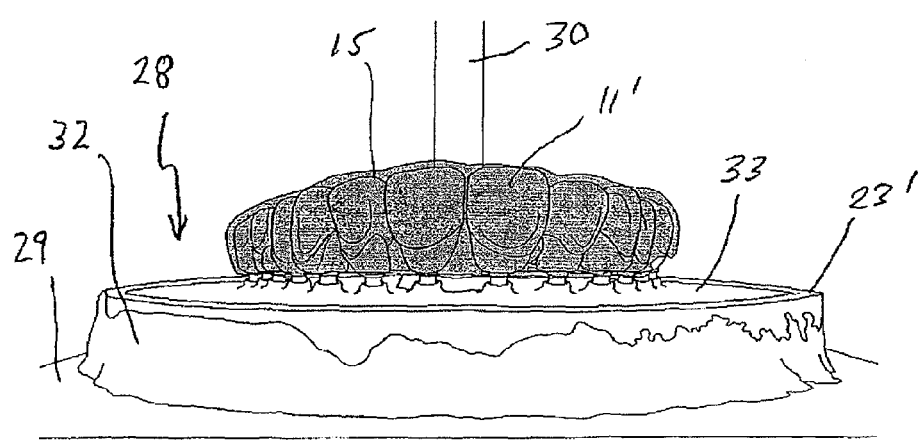
Figure 10G:
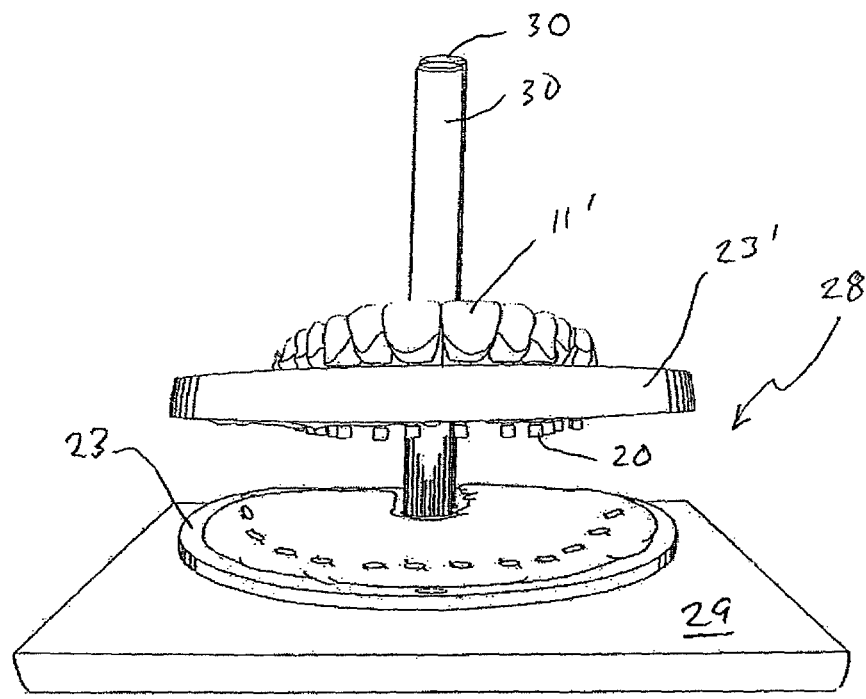
Figure 11:
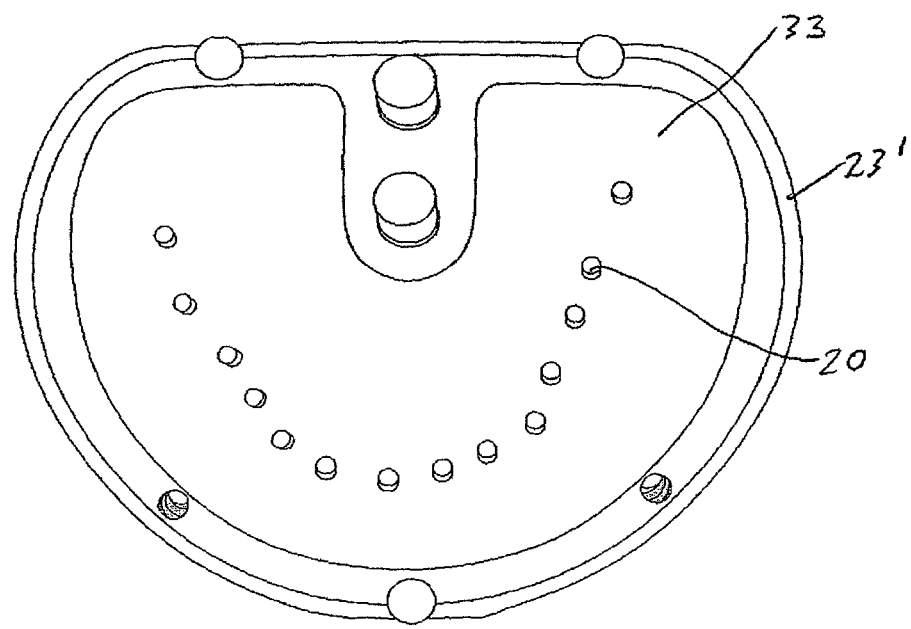
FIG. 11 shows the heads of the pins will be exposed at the end of this process shown in FIGS. 10A-10G.

A thermoplastic material 33, such as wax, is melted and poured inside the arch reconstruction frame (ARF) 23' over the alginate layer 31 in such a way that all the threaded/corrugated portions 21 of pins 19 are provided within and surrounded by molten wax 33. The wax 33 is poured up to the band part 22 of the pins 19 as shown in FIG. 10F. The wax 33 cools down after a few minutes; this cooling process can be accelerated by application of some cooling agent. Once the wax 33 cools down and gets hard, the block out material 32 which was used to seal and block the gap between two arch reconstruction frames (ARFs) is removed. The second arch reconstruction frame (ARF) 23' is taken out of the vertical articulator 28, as shown in FIGS. 10G and 11. The second arch reconstruction frame (ARF) 23' has pins 19 embedded in the wax 33 up to the band part 22 of the pins 19, while heads 20 of the pins will be exposed as the alginate 31 will not let the wax 33 come in contact with the pin heads 22 and, at the same time, the alginate 31 will not stick to the pin heads 20. This technique is termed "Pin's head exposing technique."

Figure 12A:
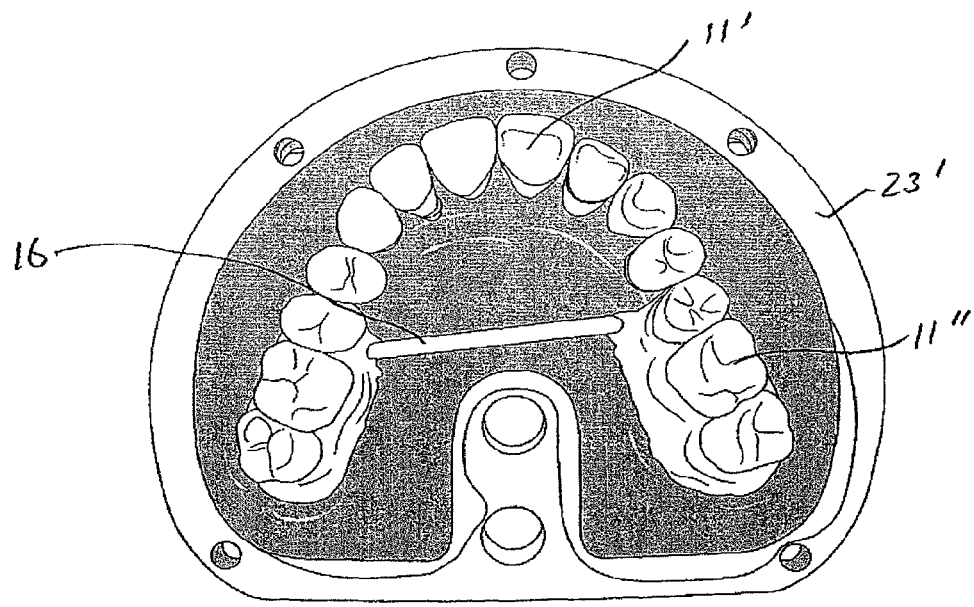
FIGS. 12A and 12B show, respectively, the whole upper arch reconstructed and position of teeth inside the patient's mouth.
Figure 12B:
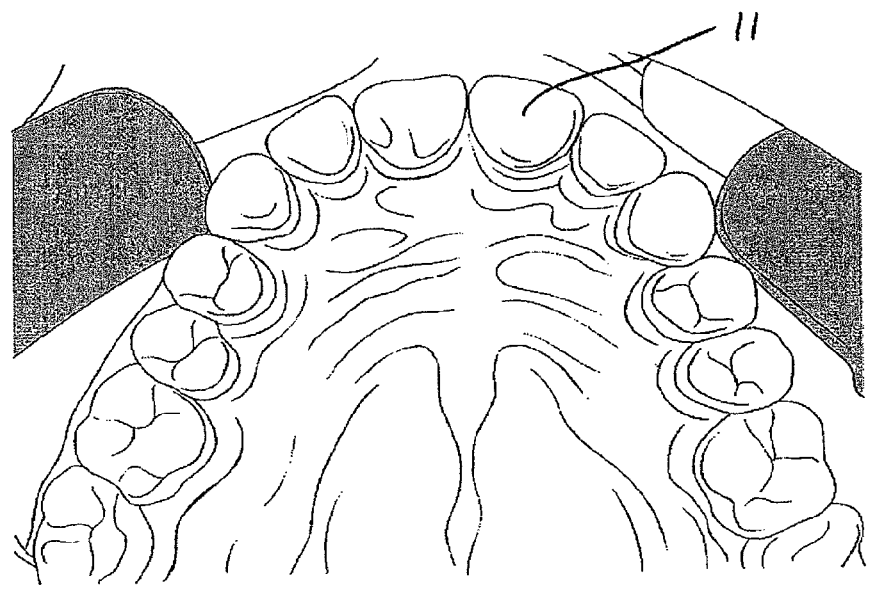

After the second arch reconstruction frame (ARF) 23' is taken out of the vertical articulator 28, the entire upper arch has been reconstructed. FIGS. 12A and 12B show, respectively, the whole upper arch reconstructed and position of teeth inside the patient's mouth. As can be seen comparing FIG. 12A with FIG. 12B, the position of teeth in the reconstructed arch achieved after going through this process will essentially be same as the position of teeth inside the patient's mouth or the position of teeth in an impression taken by the doctor (see FIG. 1). This technique is referred to herein as "Zeroing". The ZA is cut and separated from the upper reconstructed arch.

In the following discussion, bite registration means the inter-arch relationship of upper and lower teeth of the patient. An accurate bite registration is necessary to establish the proper occlusal relationship during mounting of the two arches. It is also necessary while correcting malocclusions so that teeth can be reconstructed and adjusted without creating inter-arch interferences. A negative replica of this relationship may be provided by the treating dentist or orthodontist along with the patient's impressions. In dentistry, occlusion refers to the manner in which the teeth of upper and lower arches come together when the mouth is closed.

Figure 13A:
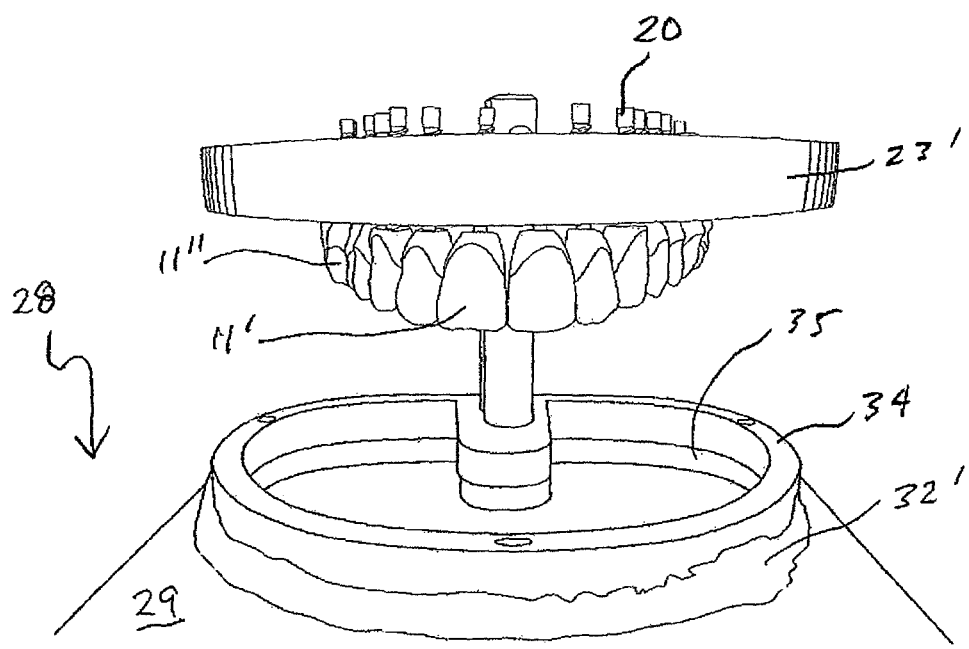
FIGS. 13A-13D show a bite registration/bite setting technique and reconstruction of the lower arch using arch reconstruction frames (ARFs) and a vertical articulator (VA).
Figure 13B:
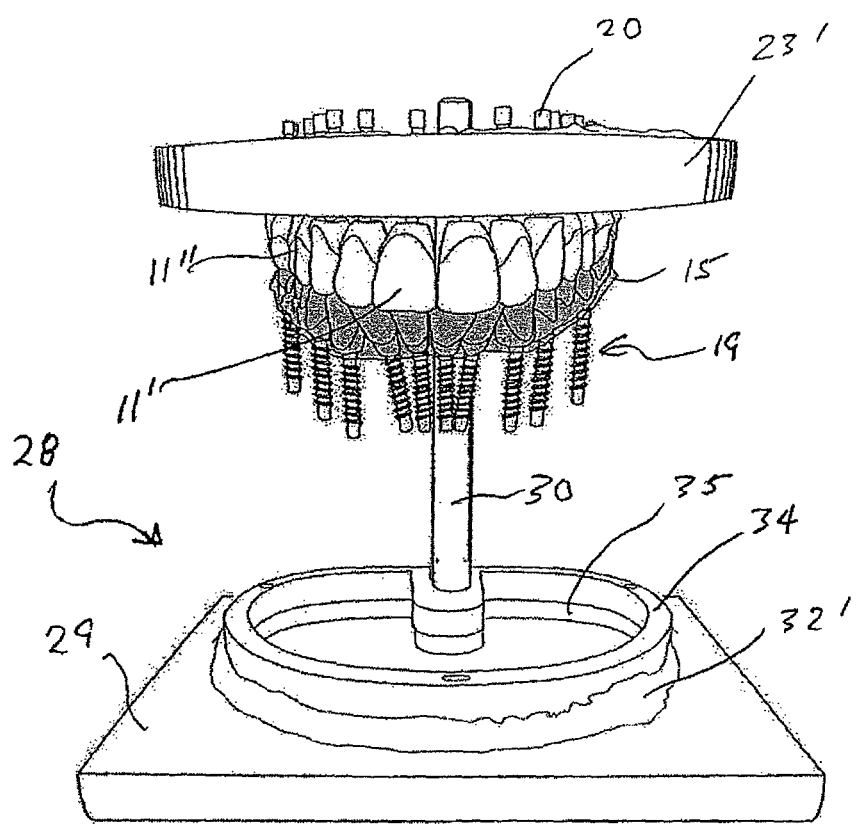

Two new arch reconstruction frames (ARFs) 34, 35 are mounted one by one at the base 29 of a vertical articulator 28. Any potential gaps between two arch reconstruction frames (ARFs) 34, 35 are sealed and blocked out, e.g., with a block out material 32'. The arch reconstruction frame (ARF) 23' having upper cast teeth 11', 11" are then placed in the vertical articulator 28 in such a way that heads of the pins 20 face upwards as shown in FIG. 13A. Then a zero aligner (ZA) 15 having lower teeth with attached pins 19 is brought in close approximation with the upper reconstructed arch held in the arch reconstruction frame (ARF) 23'. Once the desired position representing the occlusion of patient is achieved, sticky material 36 (see FIG. 13D) is used to glue the two arches in that position as shown in FIG. 13B. To maximize the accuracy of this inter-arch relationship, the patient's bite registration and photographs can be used.

Figure 13C:
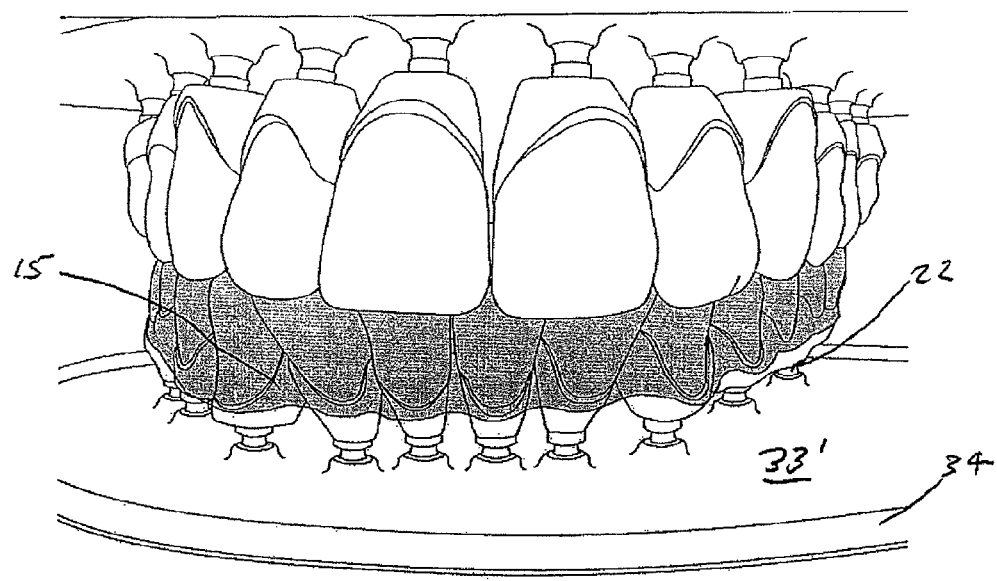
Figure 13D:
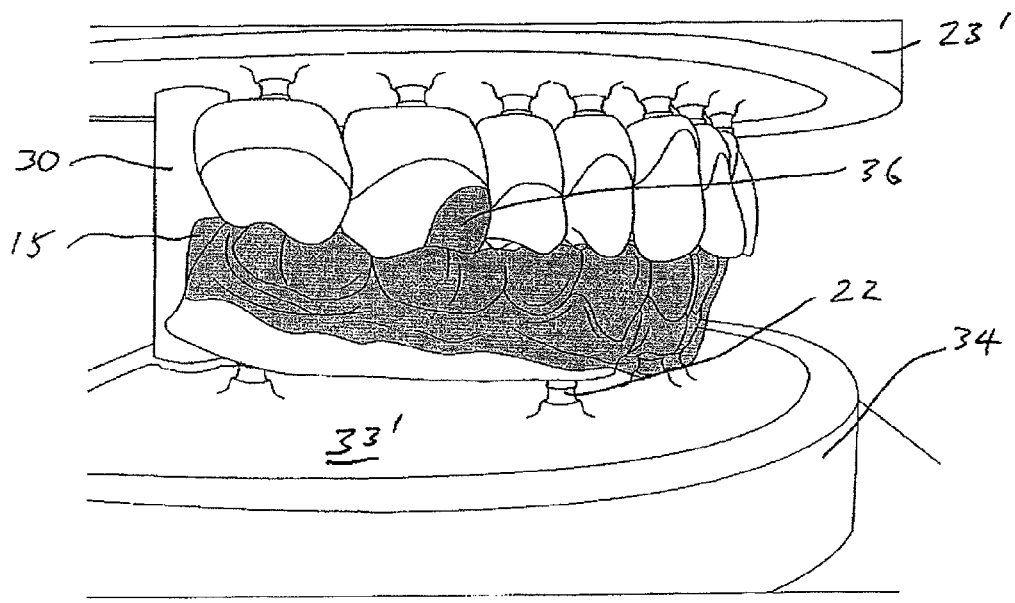
Figure 14:
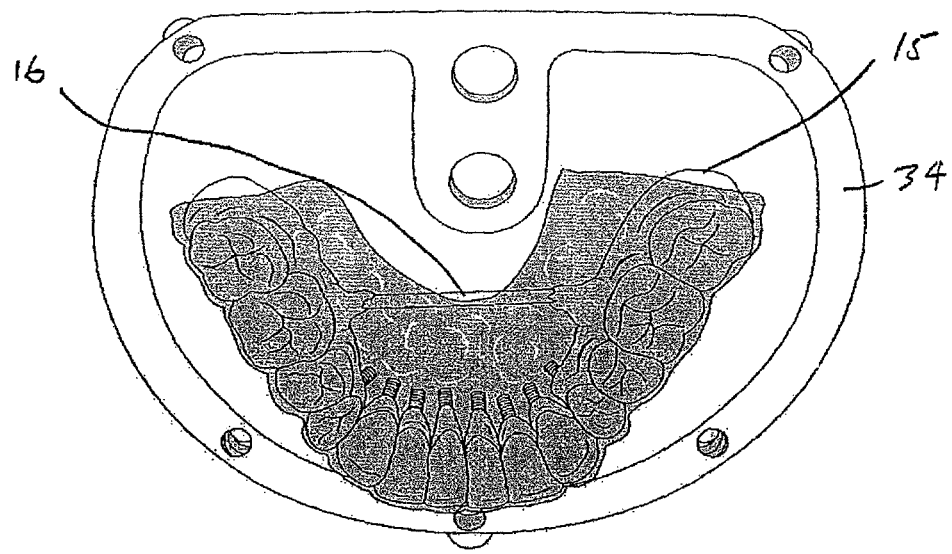
FIG. 14 shows lower arch reconstructed having zero aligner (ZA) on it at the end of the process shown in FIGS. 13A-13D.

A freshly mixed alginate layer is placed inside the arch reconstruction frame (ARF) 35 already placed at the base of the vertical articulator (VA) 28. Then, the whole assembly of upper reconstructed arch held in arch reconstruction frame (ARF) 23' along with the glued lower zero aligner (ZA) 15 having lower cast teeth in it is brought to the base of a vertical articulator 28 in such a way that heads of the pins 19 of the lower teeth dip inside the freshly mixed alginate material. Once the alginate is solidified, melted wax 33' is poured inside the arch reconstruction frame (ARF) 34 over the alginate layer in such a way that all of the threaded/corrugated portion 21 of pins 19 of the lower cast teeth are dipped inside the wax 33' and threaded/corrugated portion 21 of the pins 19 is surrounded by molten wax. The wax 33' is poured up to the band part 22 of pins 19 of lower teeth as shown in FIGS. 13C and 13D. The wax 33' cools down after a few minutes; this cooling process can be accelerated by application of some cooling agent. Once the wax 33' cools down and gets hard, the glue 36 used to unite the upper reconstructed arch held in the arch reconstruction frame (ARF) 23' and the lower zero aligner (ZA) 15 and the block out material 32' that was used to seal and block the gap between two arch reconstruction frames (ARFs) 34, 35 are removed. Upper arch reconstruction frame (ARF) is taken out of the vertical articulator leaving behind the lower reconstructed arch enclosed in lower zero aligner (ZA) 15 as shown in FIG. 14. The lower zero aligner 15 is then cut and removed from the lower reconstructed arch.

Figure 20:
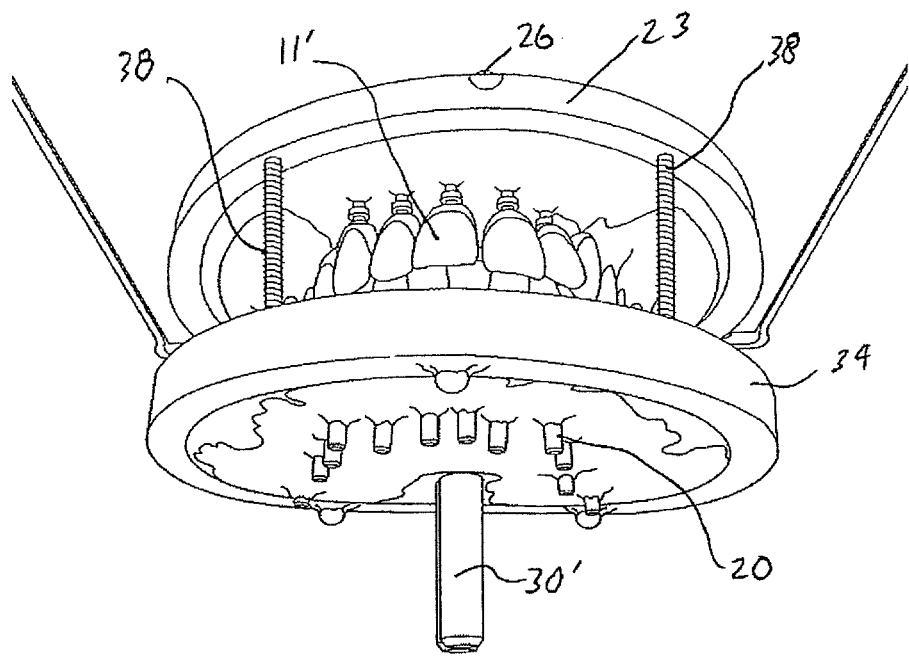
FIG. 20 shows the upper and lower reconstructed arches mounted with the help of vertical bars and magnetic/ball system on platform of a digital picture recorder (DPR).

In order to attain the same vertical position every time whenever desired, two screws 38 can be provided at the boundary of arch reconstruction frame (ARF) in screw holes 27 (see FIG. 20).

Figure 15A:
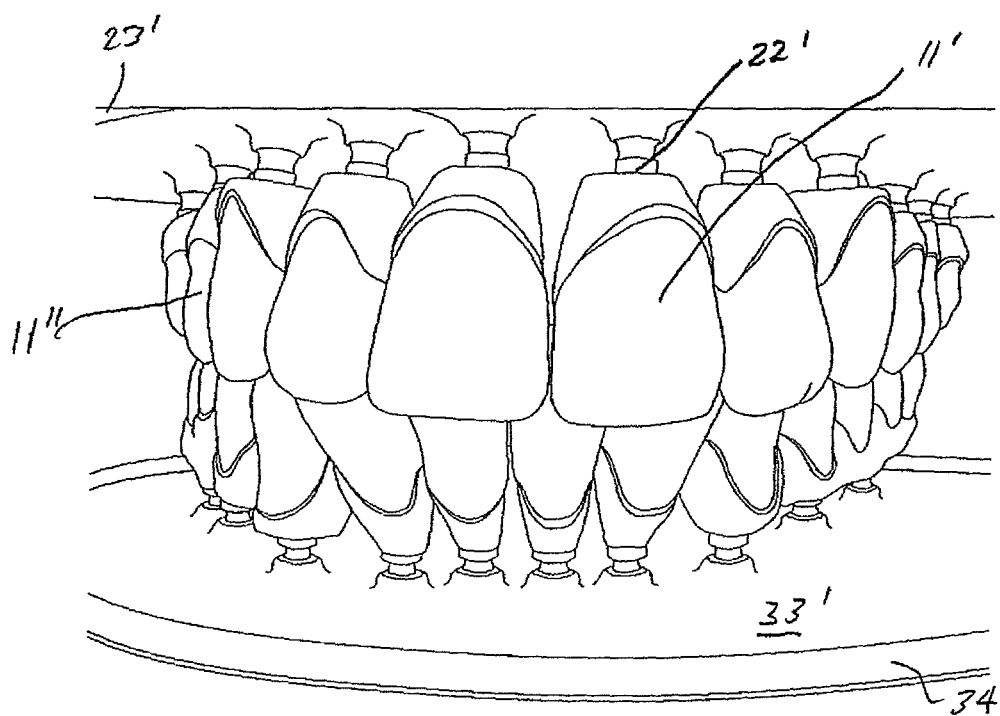
Figure 15B:
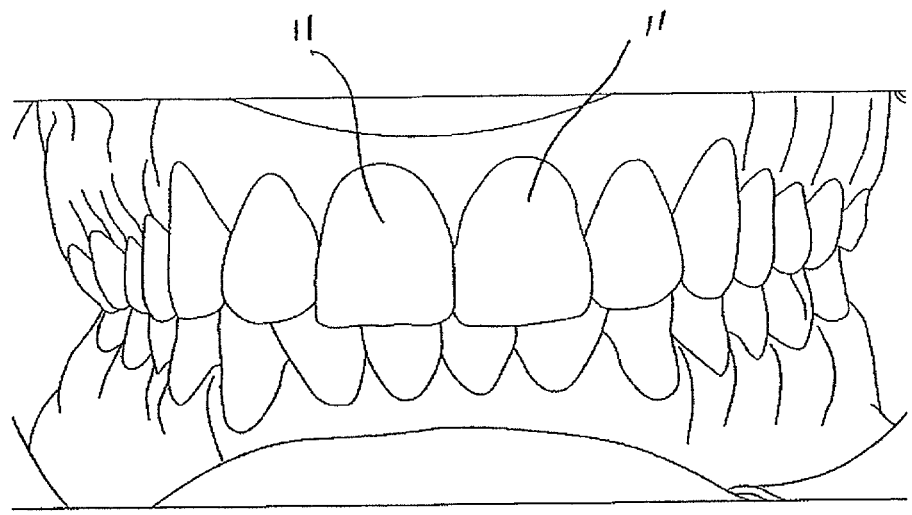
Figure 15C:
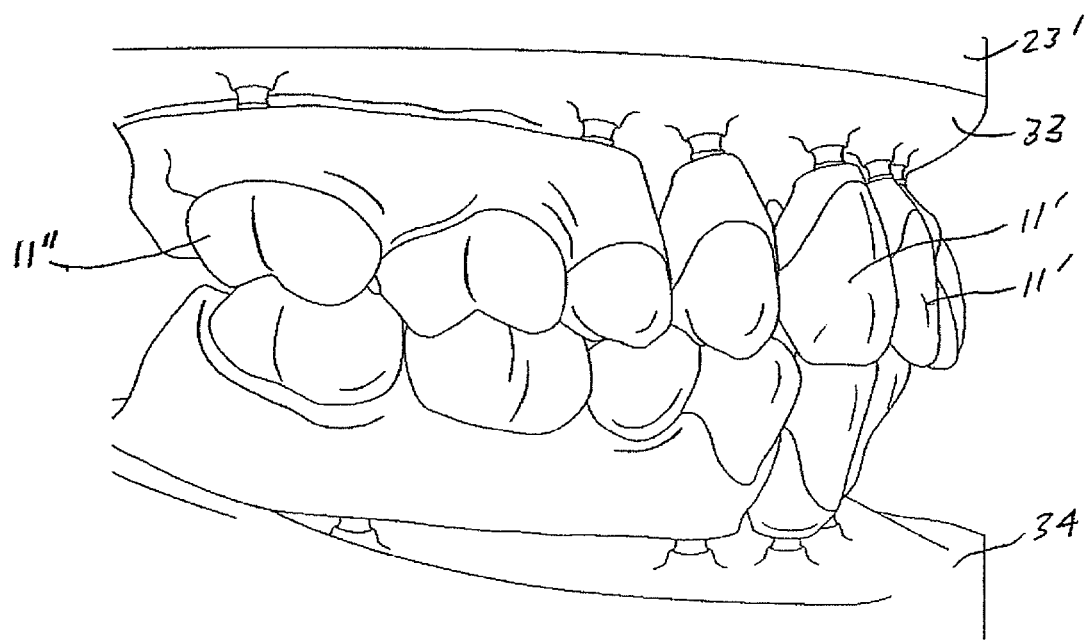
FIGS. 15C and 15D show side views, respectively, of the upper and lower processed arches together and the occlusion in the patient's mouth.
Figure 15D:
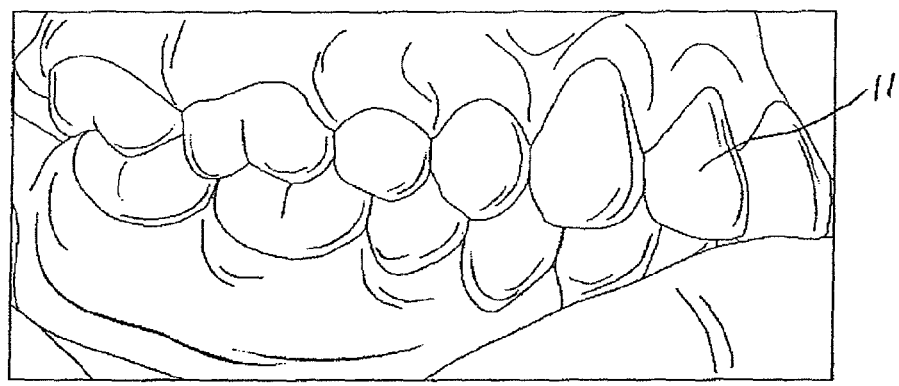

The above-described process provides upper and lower reconstructed arches, with each tooth 11' and uncut segment 11" having a pin 19, the corrugated portion 21 of pins 19 being surrounded by wax 33, 33' and heads 20 of the pins 19 exposed. Moreover, when the two arches are placed inside the vertical articulator (VA) 28, they represent the occlusion present inside the patient's mouth. The occlusion of reconstructed arches is established with the help of specially designed arch reconstruction frames (ARFs) 23', 34 and vertical articulator (VA) 28 as shown in FIGS. 15A-15D. FIGS. 15A and 15B show front views, respectively, of the upper and lower processed arches (held in arch reconstruction frames (ARFs) 23', 34) together and the occlusion in the patient's mouth while FIGS. 15C and 15D show side views, respectively, of the upper and lower processed arches (held in arch reconstruction frames (ARFs) 23', 34) together and the occlusion in the patient's mouth.

The separated teeth 11' present in wax 33, 33' can now be moved progressively to obtain their desired position (aligned position) depending on the malocclusion and as required by the treating doctor.

Figure 16:
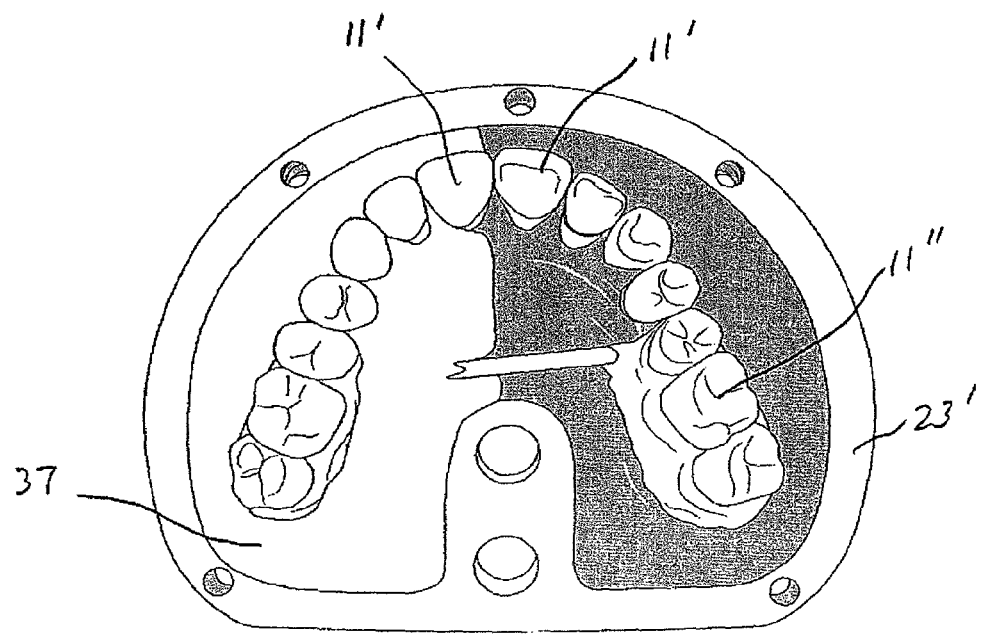
FIG. 16 shows half portion of thermoplastic material and arch (half on the left in this example) covered with insulating material.
Figure 17:
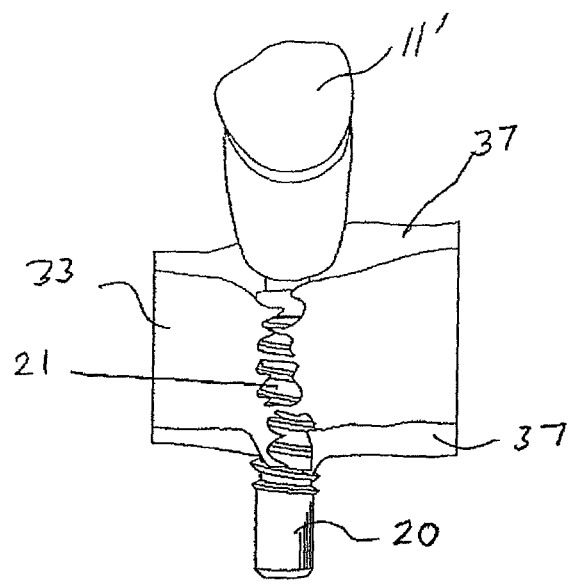
FIG. 17 shows a cross-section through the arch with an upper/top insulating layer, wax in the middle, and a lower/bottom insulating layer.

As shown in FIGS. 16 and 17, thin layer of a good insulating material 37, i.e., a thermo-resistant material (e.g., alginate or silicone material), which melts at a higher temperature than wax 33, is placed on the top and bottom exposed surfaces of wax 33 present in arch reconstruction frame (ARF) 23'. This will prevent the heat from reaching the wax 33 directly that can melt the whole wax layer especially wax present around the neighboring teeth. If the insulating layer is placed on one surface then it is named as "double layer technique" and if on both the surfaces then it is named as "triple layer technique" as shown in FIG. 17.

Figure 18A:
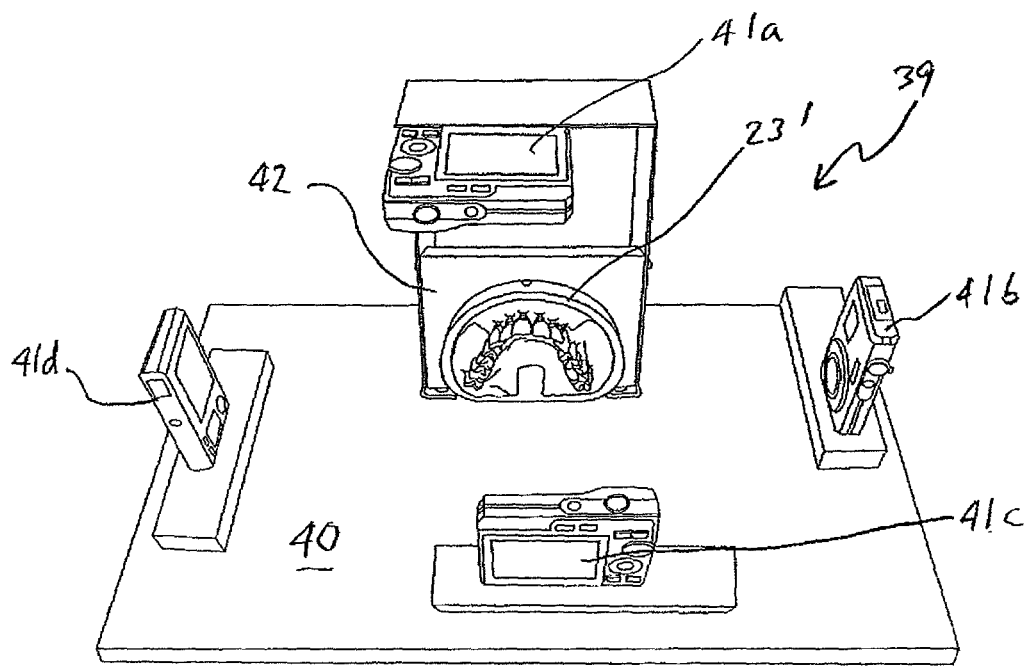
FIGS. 18A and 18B show, respectively, a top perspective view and a close perspective view of a digital picture recorder (DPR) lodged with reconstructed upper arch.
Figure 18B:
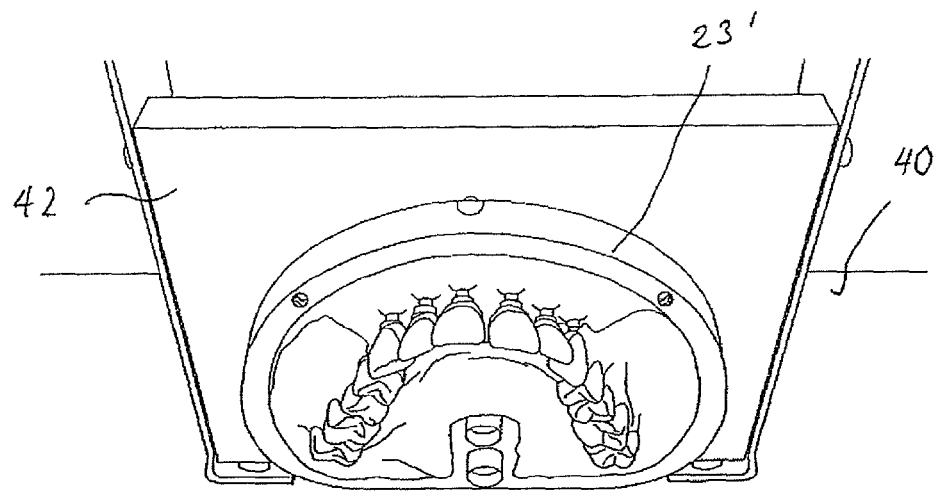
Figure 19:
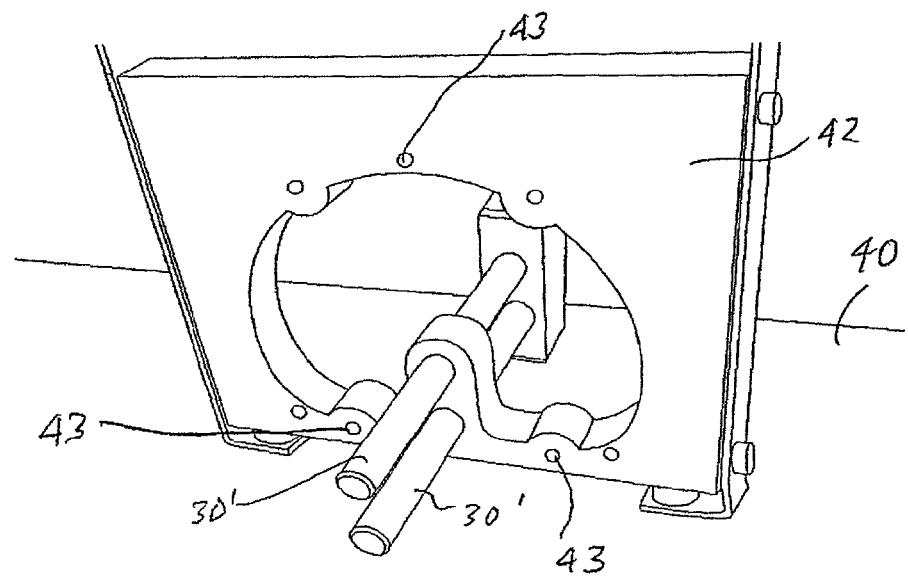
FIG. 19 shows the platform of digital picture recorder (DPR) with vertical bars and magnetic system.

In order to keep a digital picture record of the progressive movements of tooth/teeth, a Digital Picture Recorder (DPR) is used. As shown in FIGS. 18A, 18B and 19, the Digital picture Recorder (DPR) 39 has a platform 40, which supports arch reconstruction frames (ARFs) 23', 34 and one or more cameras 41a, 41b, 41c and 41d. The arch reconstruction frames (ARFs) 23', 34 and one of the cameras 41a are supported on a vertical bars platform 42. As better shown in FIG. 19, vertical bars platform 42 includes a plurality of magnets 43 that correspond in location to the balls 26 on the arch reconstruction frames (ARFs) 23', 34. This magnet/ball system 43, 26 will allow the arch reconstruction frames (ARFs) 23', 34 to be placed at the same position every time. Bars 30', 30' also provide for alignment of the arch reconstruction frames (ARFs) 23', 34 using holes 25 in the arch reconstruction frames (ARFs) 23', 34, as shown in FIGS. 19 and 20. Digital cameras 41a, 41b, 41c and 41d are placed all around the platform 40 to take the pictures from different perspective angles/views as shown in FIG. 18A.

Before giving any movement to any tooth, an arch reconstruction frame (ARF) having a reconstructed arch is placed on the platform 42 of digital picture recorder (DPR) 39 as shown in FIG. 18B. Photographs are then taken with digital cameras 41a, 41b, 41c and 41d placed around the platform 40 to take the pictures from different perspective angles/views as shown in FIG. 18A and the photographs appropriately named, e.g., as "Picture#1." The arch reconstruction frame (ARF) is then removed and desired tooth/teeth are moved using following process.

To move any tooth in a reconstructed arch, the insulating layer 37 is removed around that specific tooth. The arch reconstruction frame (ARF) containing that reconstructed arch is placed in a movement platform with heads 20 of the pins 19 exposed, e.g., facing downward. Depending upon the desired movement which can be in any one axis, a mechanical movement device is placed under that tooth in such a way that the pin's head 20 fits into the tooth fixture clamp/slot present in the mechanical movement device. Then it is locked to stabilize the whole assembly.

Figure 21A:
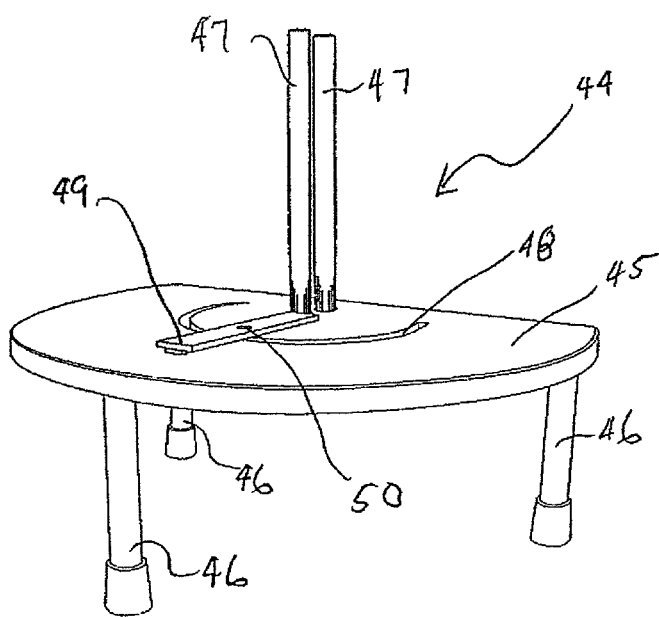
FIGS. 21A and 21B show, respectively, a side perspective view and a top perspective view of a movement platform.
Figure 21B:
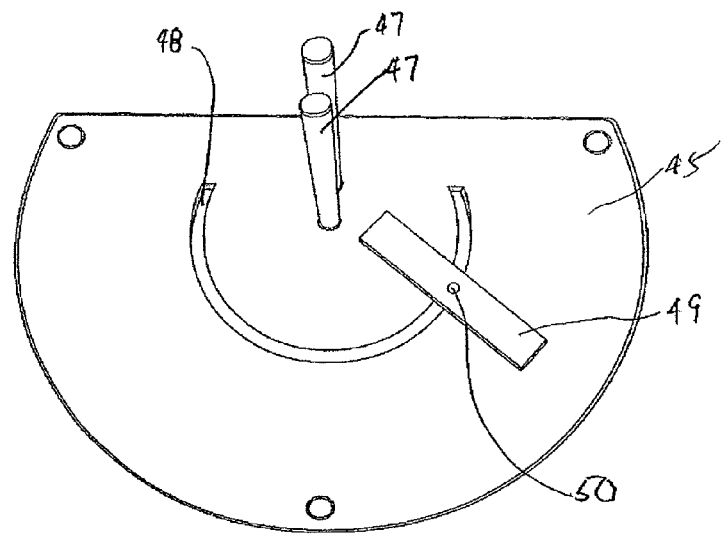

An example of a movement platform is shown in FIGS. 21A and 21B, which show, respectively, a side perspective view and a top perspective view of the movement platform 44. The movement platform 44 shown in this example is a custom made device having a base 45 supported on legs 46. Vertical bars 47, spaced a distance corresponding to the bars 30 of the vertical articulator 28, are provided to be inserted through holes 25 of an arch reconstruction frame (ARF) to hold the arch reconstruction frame (ARF) containing a reconstructed arch in place. The base 45 has a U-shaped track 48 to guide an adjustment arm 49 on which a mechanical movement device can move. The adjustment arm 49 can be locked in a desired position in the U-shaped track 48 using a locking screw 50.

Mechanical movement devices, generally designated by the reference numeral 51 (see FIGS. 22A and 22B) are customized mechanical tools designed to move an individual tooth with its associated pin fixture in either direction along or around a single axis. There are at least four types of movement tools, including a:
  i. rotational tool (for movement of tooth around long axis of its pin);
  ii. tipping tool (for movement of crown in one direction and of its pin in opposite direction);
  iii. translational tool (for bodily movement of tooth as a whole in linear plan); and
  iv. vertical correction tool (for downward/upward, i.e., intrusion/extrusion movement of tooth).

Each movement tool assembly has some basic parts which are common in all tools, although the principle design which determines the type of movement that a tool will produce varies in the different tools. In almost every tool there is a tooth fixture clamp/slot, generally designated by the reference numeral 52, which will receive and snugly engage/receive the head 20 of the pin fixture 19 coming out of the tooth 11'. Every tool has a ball bearing joint with a rotational base that provides a freedom of adjustment to the tooth fixture clamp/slot 52.

Figure 22A:
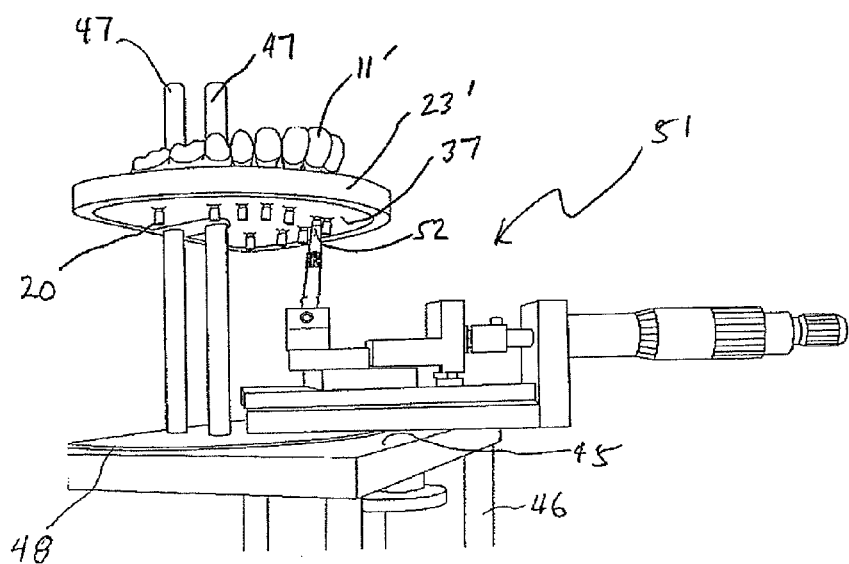
FIGS. 22A-22B show mounting teeth having pins into wax, heating and using a customized mechanical movement device to move a pin along with tooth in a measured manner in the desired direction.

As shown in FIG. 22A, an arch reconstruction frame (ARF) 23' is then slid along twin vertical bars 47 of the movement platform 44. A mechanical movement device 51 is provided on the adjustment arm 49 and the adjustment arm 49 moved along U-shaped track 48 so that head 20 of the tooth desired to be moved is aligned with the tooth fixture clamp 52 of the movement tool 51 along the long axis of pin 19 fixed to tooth 11'. The adjustment arm 49 is locked in a desired position in the U-shaped track 48 using the locking screw 50. After this visual adjustment of movement tool's passive components, the arch reconstruction frame (ARF) 23' is slid down along the twin vertical bars 47 so that pin's head 20 (of tooth desired to be moved) fits in the tooth clamp/slot fixture 52 and it is tightened.

Figure 22B:
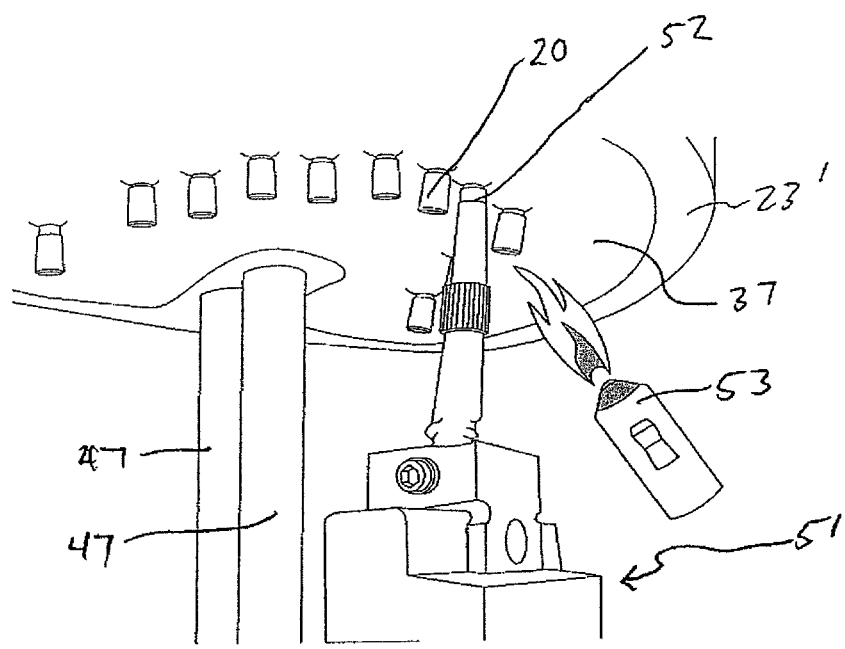

In this state, as shown in FIG. 22B, the pin 19 of the tooth 11' desired to be moved has its corrugated portion 21 surrounded by wax 33 and its head 20 fitted/locked into the tooth clamp/slot fixture 52 of the mechanical movement device 51. Heat is applied from heater 53 to the tooth fixture clamp/slot 52 of the mechanical movement device 51, which softens the wax 33 around the corrugated portion 21 of the pin 19 (as heat is transferred to the pin 19). The thin layer of insulating material 37 surrounding other pins' heads 20 will prevent heat from melting unnecessary wax.

With the help of the mechanical movement device 51, measured movement is applied to move the individual tooth into the desired direction in along or about one axis.

The wax 33 is again left for some time to cool down and then the mechanical device 51 is unlocked and removed. Upper and Lower arches are replaced in the vertical articulator and brought in close approximation with each other to check any inter-arch interferences etc.

The arch reconstruction frame (ARF) having the moved tooth/teeth is placed again on the platform 40 of a digital picture recorder (DPR) 39 and additional picture(s) taken again, e.g., named as "Picture#2." The pictures can be loaded in software that has the ability to give following benefits:
  to show the transition from one step to next step to see any unnecessary/unintentional movement of tooth/teeth
  to keep a digital picture record of the all the previous steps. Pictures taken by the above method can also be loaded in certain commercially available software for review.

The arch reconstruction frame (ARF), having moved tooth/teeth in a new position, is now placed inside the thermoforming machine to fabricate a tooth positioner on it. The top insulting layer will prevent the heat of thermoforming machine from melting unnecessary wax and will resist the air pressure as well. Tooth positioner is trimmed, finished and is worn by the patient for given time.

The same steps are repeated and next tooth positioner is made and worn by the patient till the time that desired position of tooth/teeth is achieved.

A diagnostic setup may be accomplished using the described tools and method, which is similar to the process described above and involves:
1.1. Zeroing
1.2. Arch reconstruction
1.3. Establishing bite registration/occlusion
1.4. Taking picture #1
1.5. Mounting on the movement platform
1.6. Moving one or more tooth/teeth using different movement tools
1.7. Taking picture #2

The only differences from the process for making the tooth positioner described above is that optionally the type of casting material used can differ (less expensive casting materials such as plaster can be used in this diagnostic setup process), the amount of movement which is given through the movement devices (the cast tooth/teeth is/are moved to the desired positions) and, as this is a diagnostic setup for review only, no tooth positioner is made. Rather, the pictures can be uploaded in a flash based software program which morphs the two pictures so that they can be reviewed to see if the goals set by the treating doctor/orthodontist are achieved, keeping in mind all the basic principles of orthodontics.

Examples of mechanical movement devices are shown in FIGS. 23A-23F.

Figure 23A:
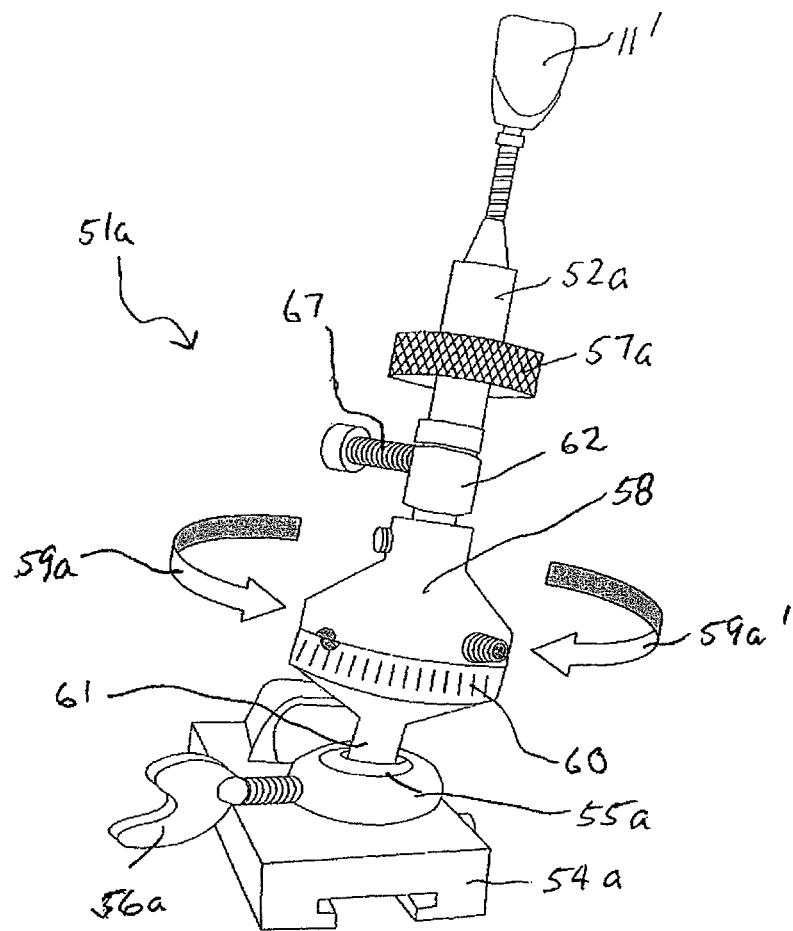
FIGS. 23A-23F show examples of mechanical movement devices.

FIG. 23A shows an example of the rotational mechanical movement device 51*a*. The rotational mechanical movement device 51*a* includes a sliding base 54*a* into which the adjustment arm 49 of the movement platform 44 is inserted. A ball bearing joint 55*a* helps the tooth fixture clamp 52*a* to align in the same axis as that of the head 20 of the pin 19 and its associated tooth 11'. The ball bearing joint 55*a* is locked with the help of locking key 56*a*. The clamp adjustment wheel 57*a* is used to tighten the tooth fixture clamp 52*a* around a head 20 of a pin 19. The rotational base 58 is rotatable about a longitudinal axis of the tooth fixture clamp 52*a* and the rotational base 58 in the direction of the arrows 59*a* or 59*a'*. A gauge wheel 60 is provided to help to determine the amount of movement given. A connecting rod 61 connects the gauge wheel 60 to the ball bearing joint 55*a* and a connecting bar 62 connects the tooth fixture clamp 52*a* to the rotational base 58. A screw 67 is provided for easy handling of the device. Rotating the rotational base 58 and the tooth fixture clamp 52*a* about their longitudinal axis in the direction of the arrows 59*a* or 59*a'* gives rotational movement to a cast tooth 11'.

Figure 23B:
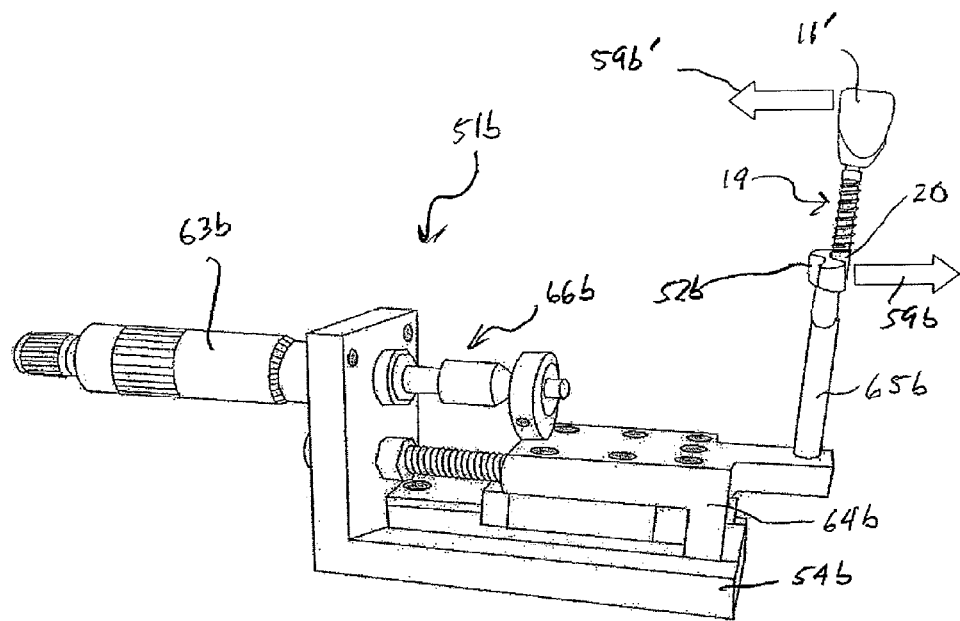
Figure 23C:
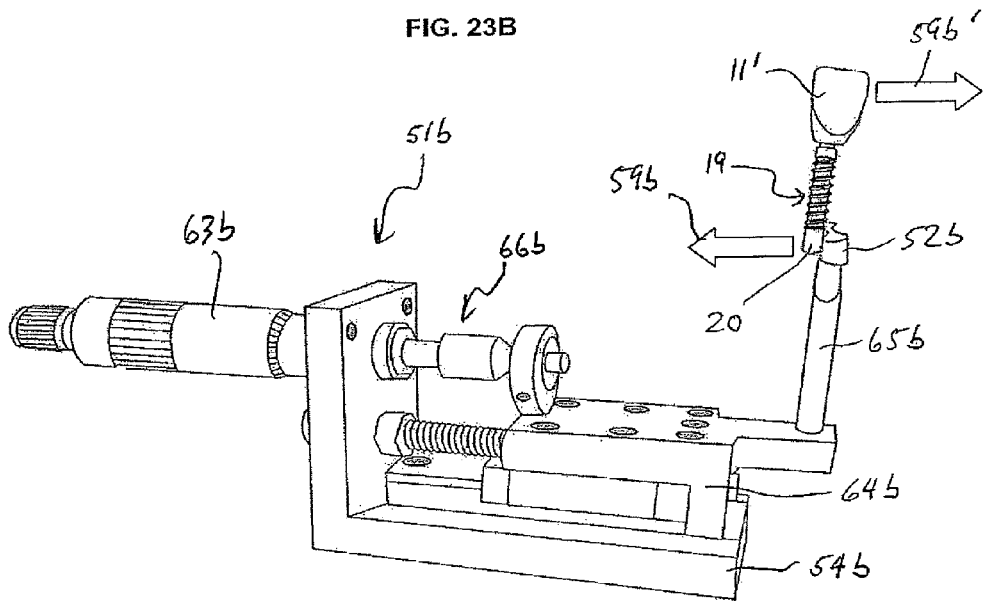

FIGS. 23B and 23C show an example of a tipping mechanical movement device 51*b*. The tipping mechanical movement device 51*b* includes a sliding base 54*b* into which the adjustment arm 49 of the movement platform 44 is inserted. Thus, sliding base 54*b* is fixed in position with respect to the base 45 by being fixed to adjustment arm 49 in U-shaped track 48 with the help of locking screw 50. A tooth fixture slot element 52*b* is shaped to receive, in slots provided on two opposite sides thereof, the head 20 of the pin 19 of the associated tooth 11' that is to be moved. The slots of the tooth fixture slot element 52*b* do not enclose pin's head 20; rather each slot just pushes the pin's head 20 in any given direction to generate a rotational movement in which crown 17 and pin's head 20 move in opposite directions. The tooth fixture slot element 52*b* is attached to a sliding platform 64*b* by a primary engaging bar 65*b*. When gauged handle 63*b* is rotated it will move the sliding platform 64*b* in linear direction along and with respect to the sliding base 54*b* through action of mechanism 66*b*. Movement given to the sliding platform 64*b* will be transferred in the primary engaging bar 65*b* and tooth fixture slot element 52*b* as they are attached with the sliding platform 64*b*. This will push the head 20 of the pin 19 in one direction with out any counter acting force at the opposing end, causing the crown 17 and pin's head 20 to move in opposite directions as shown by arrows 59*b*, 59*b'*. Measurement present on the gauged handle 63*b* will enable to determine the extent of movement. Of course, as shown in FIG. 23C, by using the slot on the opposite side from that shown being used in FIG. 23B, the crown 17 and head 20 can be made to move in opposite directions (shown by arrows 59*b*, 59*b'*) opposite to those in FIG. 23B.

Figure 23D:
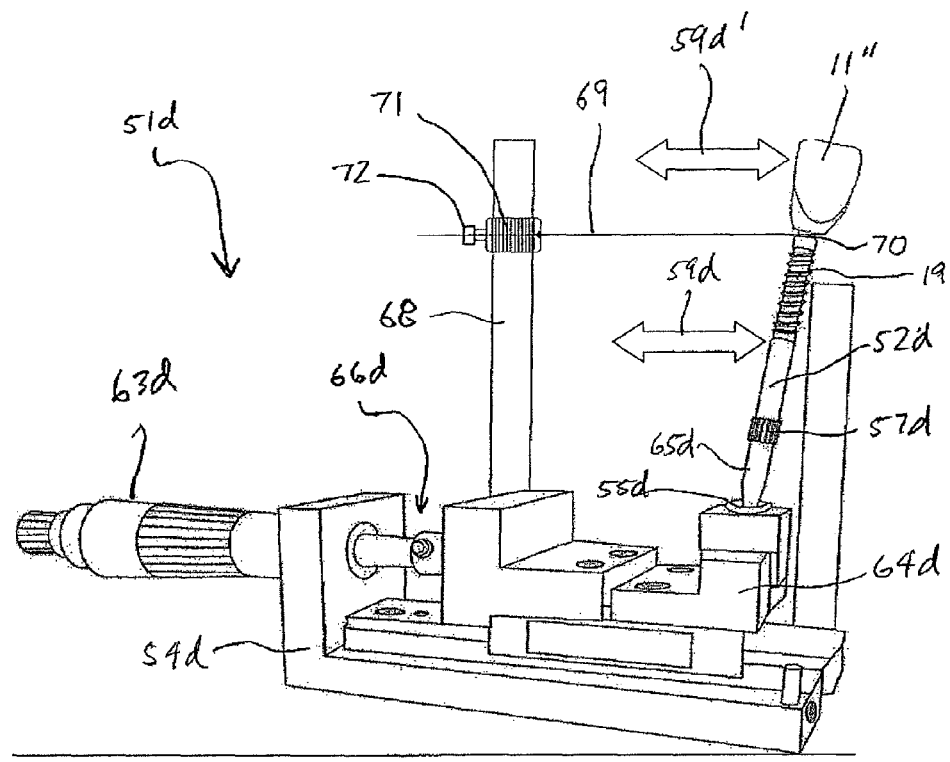

FIG. 23D shows an example of a translational mechanical movement device 51*d*. The translational mechanical movement device 51*d* includes a sliding base 54*d* into which the adjustment arm 49 of the movement platform 44 is inserted. A tooth fixture clamp 52*d* receives and clamps the head 20 of the pin 19 of the associated tooth 11' that is to be moved. The clamp adjustment wheel 57*d* is used to tighten the tooth fixture clamp 52*d* around a head 20 of a pin 19. The tooth fixture clamp 52*d* is attached to a sliding platform 64*d* by primary engaging bar 65*d* and a ball bearing joint 55*d*. When gauged handle 63*d* is rotated it will move the sliding platform 64*d* in linear direction along the sliding base 54*d* through action of mechanism 66*d*. Movement given to the sliding platform 64*d* will be transferred in the primary engaging bar 65*d* and tooth fixture clamp 52*d* as they are attached with the sliding platform 64*d*. Since the tooth fixture clamp 52*d* is locked with the help of clamp adjustment wheel 57*d*, the whole pin 19 is translated along with the tooth 11' in the direction of arrows 59*d* and 59*d'*. A pillar 68 is fixed on top surface of the sliding platform 64*d*. A connector 69 with U-shaped hook 70 can be placed into a slot in a vertical adjustable holder 71 with locking screw 72 present on the pillar 68, which is adjustable vertically. The length of connector 69 can also be changed horizontally to reach to the neck part 22" of the post 19. Once the whole assembly is locked, connector 68 with a U-shaped hook 70 at its end is placed in the neck part 22' of the pin 19. This will help to achieve the movement of pin 19 and tooth 11' as a whole in the same direction. The translational mechanical movement device 51*d* can be used without this connector 69, but without connector 69 there may be a possibility that the cast tooth 11' will lag behind the head 20 of pin 19 which is firmly gripped in the pin fixture clamp 52*d*. Measurement present on the gauged handle 63*d* will enable to determine the extent of movement.

Figure 23E:
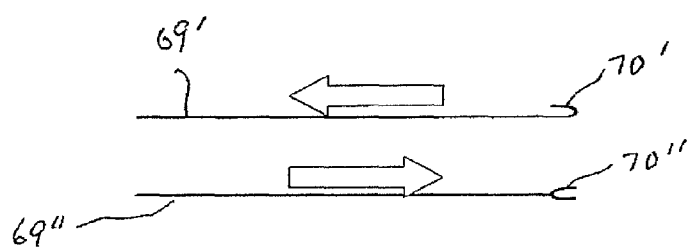

FIG. 23E shows two different connectors 69', 69" for the translational mechanical movement device 51*d* shown in FIG. 23D. Each connector 69', 69" includes a U-shaped hook 70', 70", the connector 69', 69" being chosen according to the direction of movement desired as shown by the arrows.

Figure 23F:
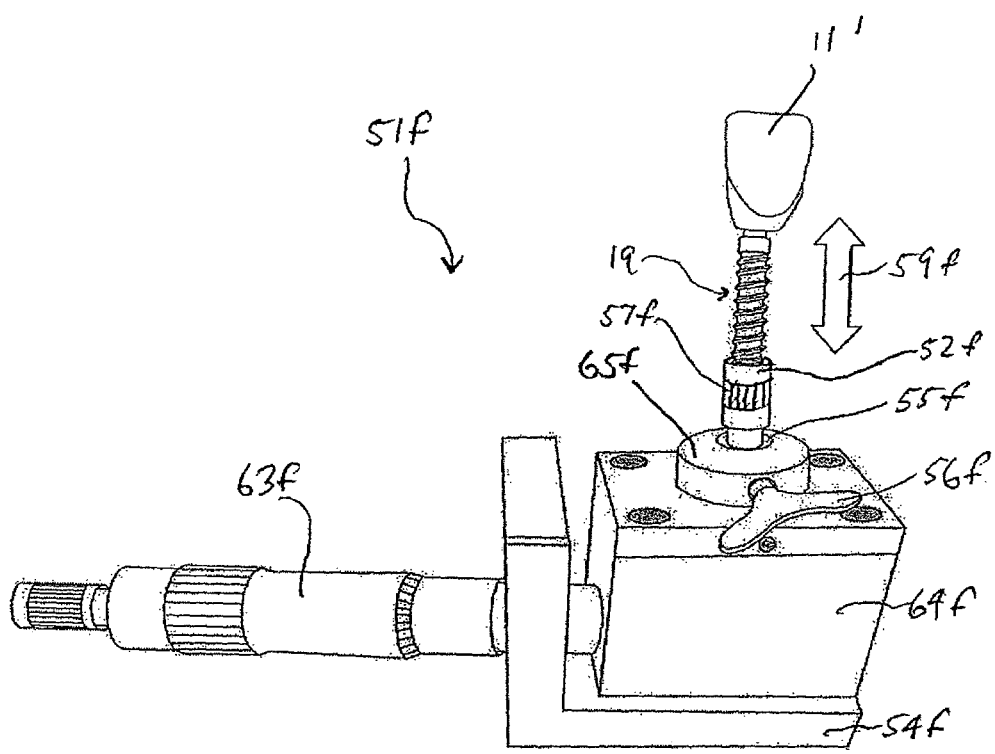

FIG. 23F shows an example of a vertical correction mechanical movement device 51*f*. The vertical correction mechanical movement device 51*f* includes a sliding base 54*f* into which the adjustment arm 49 of the movement platform 44 is inserted. A tooth fixture clamp 52*f* receives and clamps the head 20 of the pin 19 of the associated tooth 11' that is to be moved. Ball bearing joint 55*f* will help the tooth fixture clamp 52*f* to align in the same axis as that of the pin fixture 19 and its associated tooth 11'. Ball bearing joint 55*f* is locked with the help of its locking key 56*f*. The head 20 is tightened and locked in the tooth fixture clamp 52*f* with the clamp adjustment wheel 57*f*. When gauged handle 63*f* is rotated (clockwise/anti-clockwise) it will move the sliding cylinder 65*f* in downward/upward direction by a mechanism (not shown). Since the tooth fixture clamp 52*f* is locked with on the head 20, the whole pin 19 is translated along with the tooth 11' downwards or upwards as shown by the arrow 59*f*. Measurement present on the gauged handle 63*f* will enable to determine the extent of movement.

The present invention provides an improved way to replicate the initial position of the patient's dentition without any chances of adding any error. It also provides an accurate and precise movement to a tooth in an intended direction using mechanical devices capable of moving tooth in a measured manner in at least one direction in or about only one axis. Such movements combined over a number of tooth positioners manufactured following movements given through mechanical devices will correct malocclusion as planned. Another improvement in the present invention is addition of two insulating layers around the thermoplastic layer (which holds the teeth) which provides insulation and stability to the setup at initial and during the course of treatment. The present invention also provides a provision of digital visualization of the patient's dentition using initial images of the patient's dentition from different perspectives and images during and at the proposed end of treatment from different perspectives, morphing these to show the transition of treatment and proposed final correction of malocclusion. This gives the treating practitioner and patient an opportunity to view, change or accept the proposed treatment outcome before it is incorporated in the active appliance.

While the accompanying figure shows and this description describe some embodiments of the invention, the invention is not limited thereto. One skilled in the art will understand that numerous variations and modifications are possible without departing from the spirit and scope of the invention defined by the following claim(s).

I claim:

1. A method for forming a tooth positioner for repositioning at least one tooth of a patient comprising:
   providing a dental arch cast of a patient having at least one tooth to be repositioned;
   separating at least one tooth from the dental arch cast, including the at least one tooth to be repositioned to provide at least one separated cast tooth having a crown part, and a stump representing a root;
   fixing a tail end of a pin in the stump part of the at least one separated tooth, and in any non-separated teeth portions, each of the pins having a body portion and a head end extending outwardly from the stump part;
   reconstructing the dental arch cast of the patient by first aligning the at least one separated tooth to correspond to the alignment in the patient's mouth to form an aligned arch by forming a shell over the dental arch cast of a patient to provide a zero aligner having a shape corresponding to the dental arch cast of the patient, and aligning the at least one separated tooth in the zero aligner, and then providing a material around the body portion of the pins to hold the body portion of the pins in the material, wherein the head ends of the pins extend outwardly of the material, the material allowing movement of the pins when force is applied to at least the head end of the pin;
   then applying force to at least the head end of the pin fixed in the at least one tooth to be repositioned to move the at least one tooth to be repositioned in a desired direction to obtain a realigned arch; and
   then forming a tooth positioner corresponding to the realigned arch.

2. The method according to claim 1, wherein applying force to at least the head end of the pin fixed in the at least one tooth to be repositioned comprises applying force to a head of the pin to move the pin in either direction along or around a single axis to move the at least one tooth to be repositioned in a desired direction to obtain a realigned arch.

3. A method for reviewing a diagnostic setup for an orthodontic treatment, comprising:
   providing a dental arch cast of a patient having at least one tooth to be repositioned;
   separating at least one tooth from the dental arch cast, including the at least one tooth to be repositioned to provide at least one separated cast tooth having a crown part, and a stump representing a root;
   fixing a tail end of a pin in the stump part of the at least one separated tooth, and in any non-separated teeth portions, each of the pins having a body portion and a head end extending outwardly from the stump part;
   reconstructing the dental arch cast of the patient by first aligning the at least one separated tooth to correspond to the alignment in the patient's mouth to form an aligned arch by forming a shell over the dental arch cast of a patient to provide a zero aligner having a shape corresponding to the dental arch cast of the patient, and aligning the at least one separated tooth in the zero aligner, and then providing a material around the body portion of the pins to hold the body portion of the pins in the material, wherein the head ends of the pins extend outwardly of the material, the material allowing movement of the pins when force is applied to at least the head end of the pin;
   taking a first photograph of the reconstructed dental arch cast;
   then applying force to at least the head end of the pin fixed in the at least one tooth to be repositioned to move the at least one tooth to be repositioned in a desired direction to obtain a realigned arch;
   taking a second photograph of the realigned arch;
   morphing the first and second photographs; and
   reviewing the morphed photographs to review a diagnostic setup for an orthodontic treatment.

* * * * *